(12) United States Patent
Strohkirch et al.

(10) Patent No.: US 12,303,174 B2
(45) Date of Patent: May 20, 2025

(54) IMPLANT WITH INTRAMEDULLARY PORTION AND VARIABLE ANGLE EXTRAMEDULLARY PORTION

(71) Applicant: Wright Medical Technology, Inc., Memphis, TN (US)

(72) Inventors: Terrance W. Strohkirch, Memphis, TN (US); Brian Robert Thoren, Memphis, TN (US); Erin Muller, Fort Wayne, IN (US); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 449 days.

(21) Appl. No.: 17/754,918

(22) PCT Filed: Sep. 16, 2020

(86) PCT No.: PCT/US2020/050978
§ 371 (c)(1),
(2) Date: Apr. 15, 2022

(87) PCT Pub. No.: WO2021/126326
PCT Pub. Date: Jun. 24, 2021

(65) Prior Publication Data
US 2023/0218322 A1  Jul. 13, 2023

Related U.S. Application Data

(60) Provisional application No. 62/950,245, filed on Dec. 19, 2019.

(51) Int. Cl.
A61B 17/72 (2006.01)
A61B 17/80 (2006.01)
A61B 17/56 (2006.01)

(52) U.S. Cl.
CPC ...... *A61B 17/7291* (2013.01); *A61B 17/7233* (2013.01); *A61B 17/8061* (2013.01); *A61B 2017/565* (2013.01)

(58) Field of Classification Search
CPC ............................................. A61B 17/72–7291
See application file for complete search history.

(56) References Cited

U.S. PATENT DOCUMENTS 9,907,562 B2  3/2018  DaCosta et al.
2007/0142921 A1  6/2007  Lewis et al.
(Continued)

FOREIGN PATENT DOCUMENTS

CN  106037915 B  1/2019
EP  2228026 A1  9/2010
(Continued)

OTHER PUBLICATIONS

International Search Report and Written Opinion for PCT/US2020/050978 issued Feb. 25, 2021, 12 pages.
(Continued)

*Primary Examiner* — Ellen C Hammond
(74) *Attorney, Agent, or Firm* — DUANE MORRIS LLP

(57) ABSTRACT

In one aspect, an implant configured to attach a first bone section to a second bone section comprises an intramedullary portion and an extramedullary portion. The intramedullary portion is configured for insertion into the first bone section. The extramedullary portion is configured to abut a surface of the second bone section and includes a first fastener aperture configured to receive a bone fastener inserted in the second bone section. The intramedullary portion and the extramedullary portion are coupled such that the extramedullary portion is rotatable with respect to the intramedullary portion.

17 Claims, 29 Drawing Sheets

(56) References Cited

U.S. PATENT DOCUMENTS

2019/0125418 A1  5/2019 Muller et al.
2019/0307495 A1  10/2019 Geldwert

FOREIGN PATENT DOCUMENTS

| | | |
|---|---|---|
| EP | 2624771 B1 | 12/2015 |
| EP | 2806831 B1 | 7/2017 |
| FR | 2948555 A1 | 2/2011 |
| GB | 191229174 A | 1/1913 |
| IT | BA20130009 U1 | 9/2014 |
| WO | 2013022876 A1 | 2/2013 |
| WO | 2021086176 A1 | 5/2021 |
| WO | WO-2021123994 A1 * | 6/2021 |

OTHER PUBLICATIONS

Partial Supplementary European Search Report issued in connection with corresponding European Patent Application No. 20901874.6, Sep. 12, 2023, 15 pages.

Extended European Search Report issued in connection with corresponding European Patent Application No. 20901874.6, Dec. 15, 2023, 13 pages.

* cited by examiner

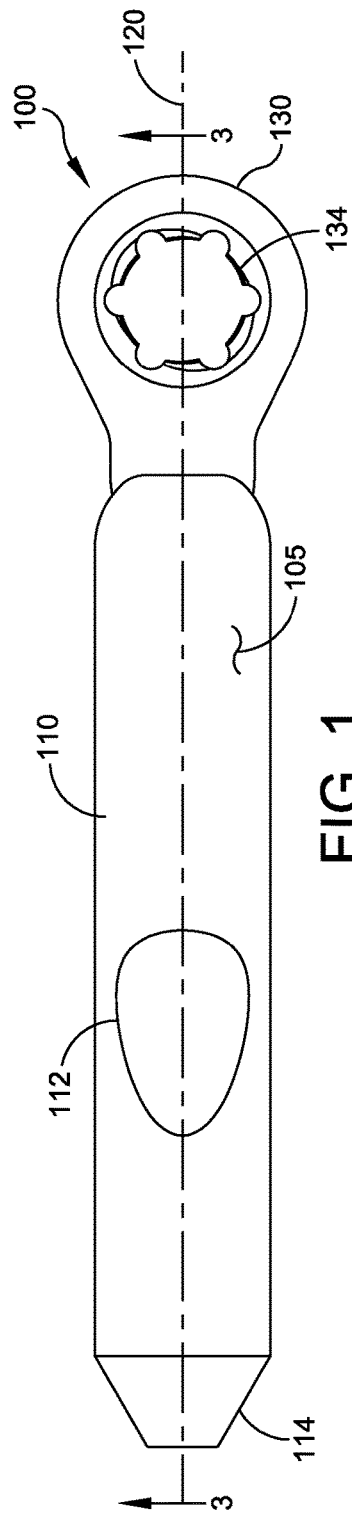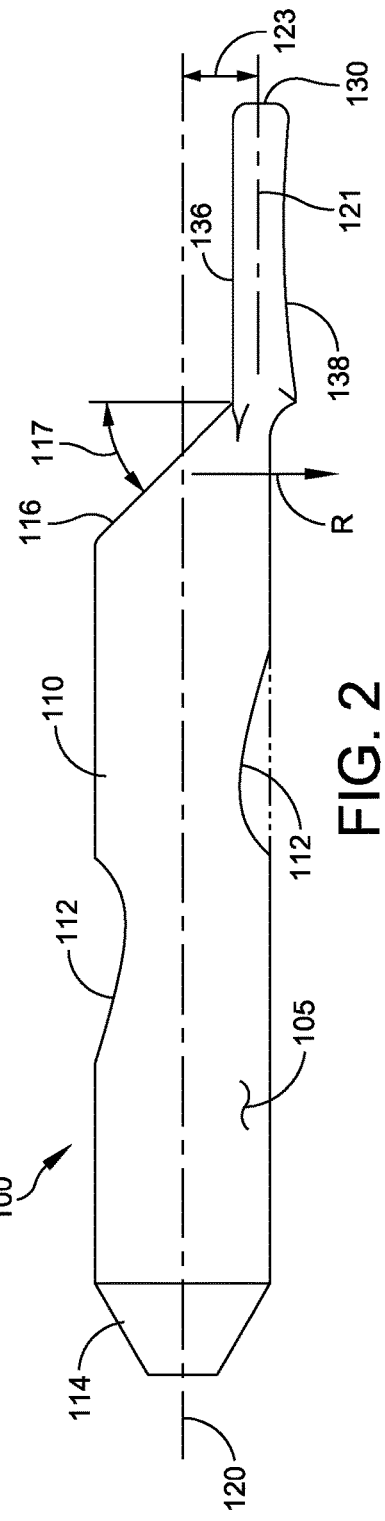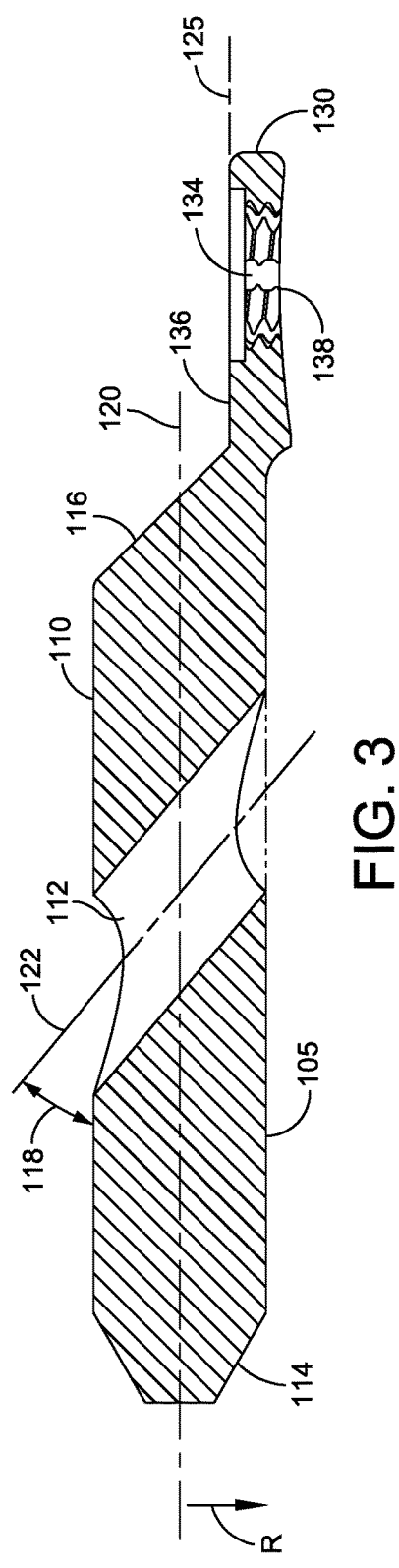

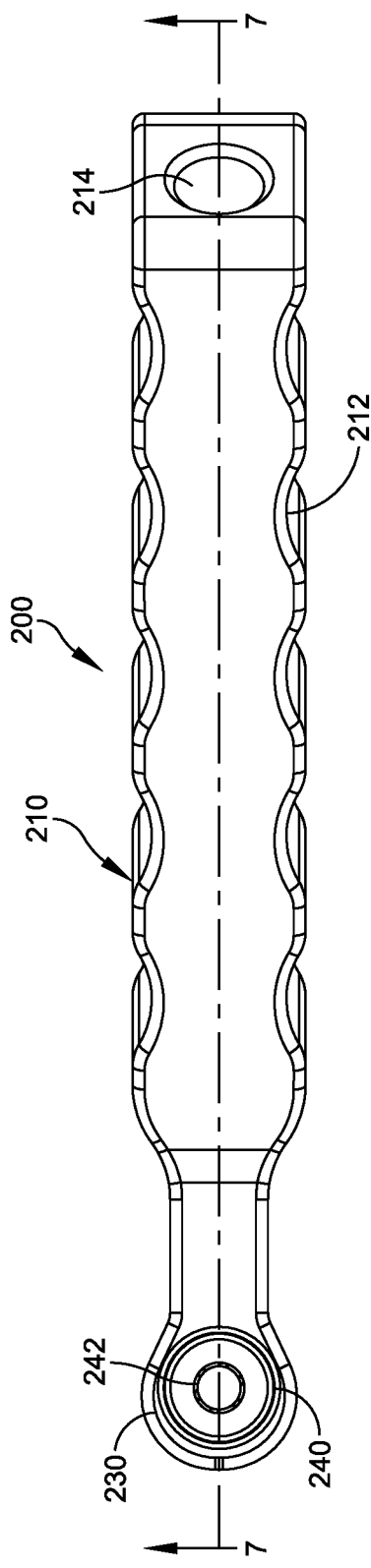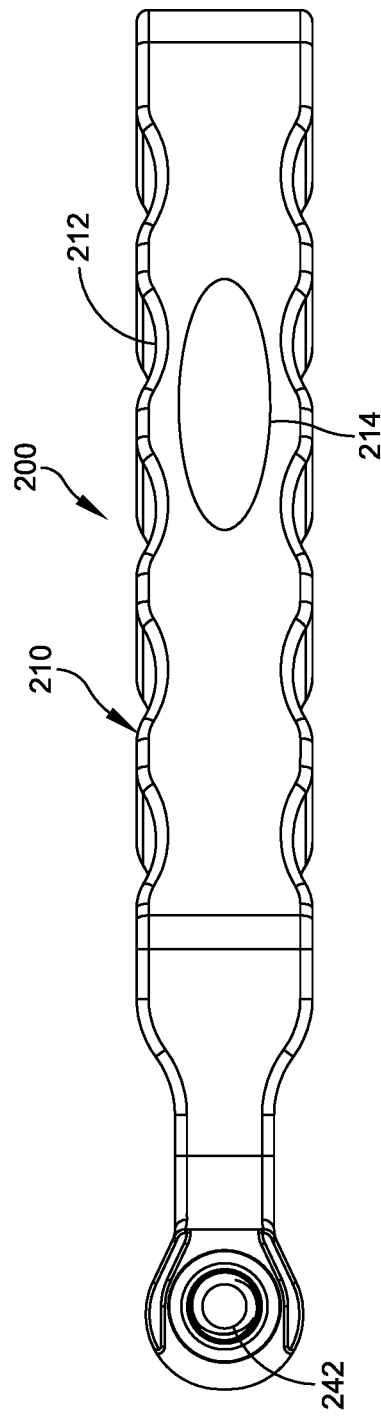

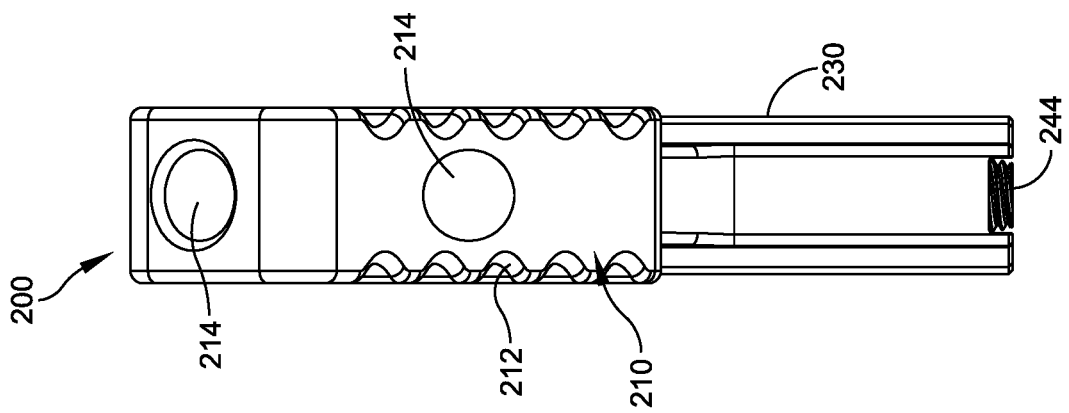
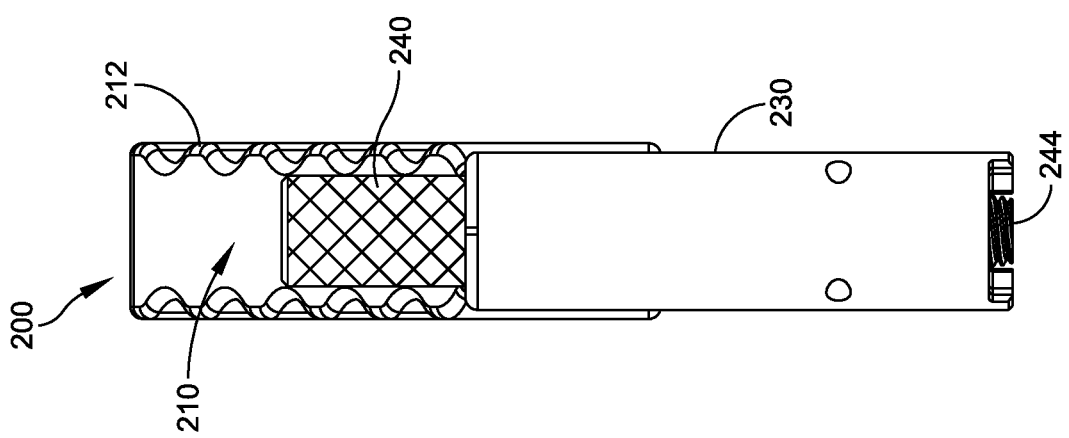

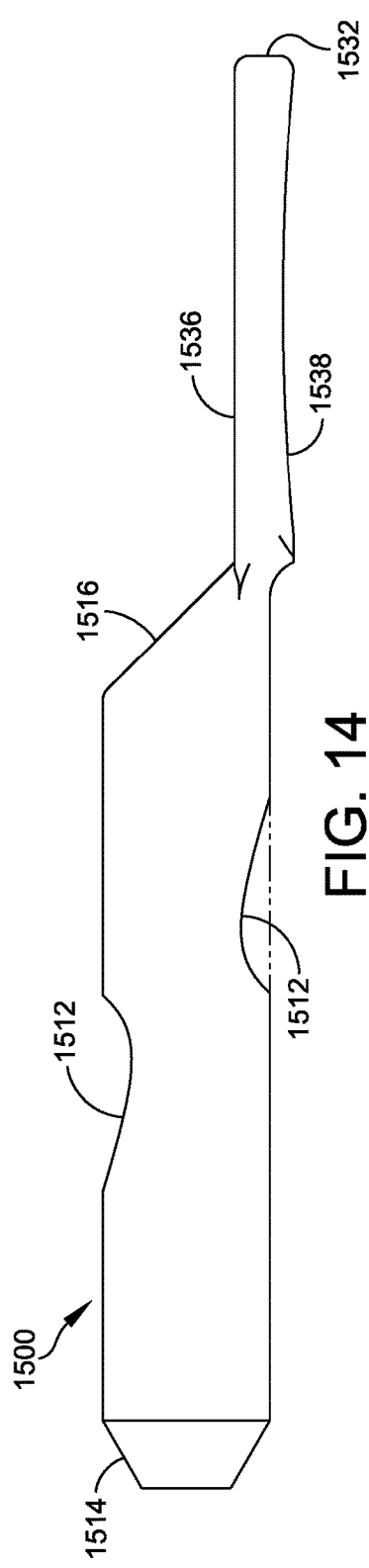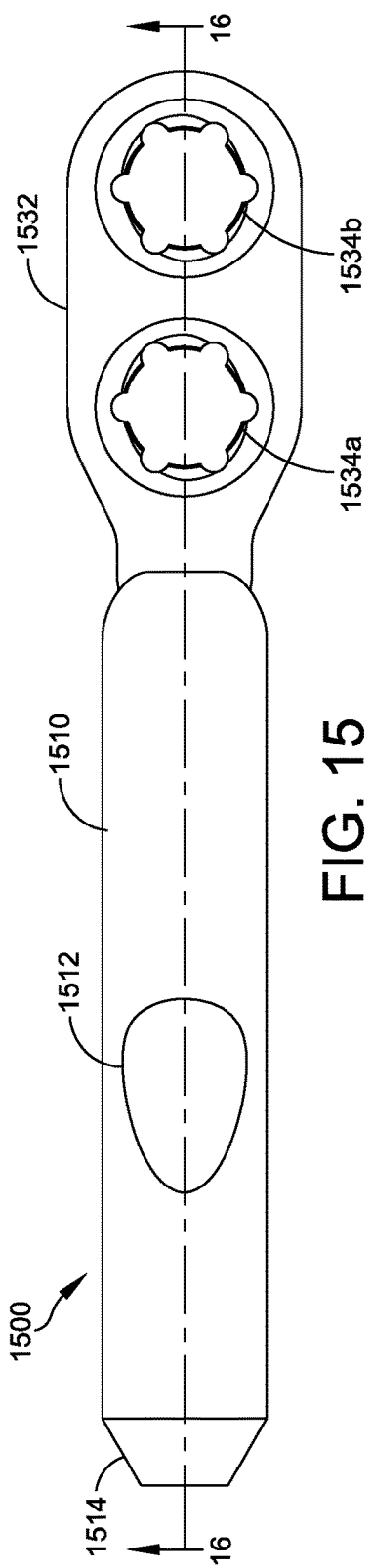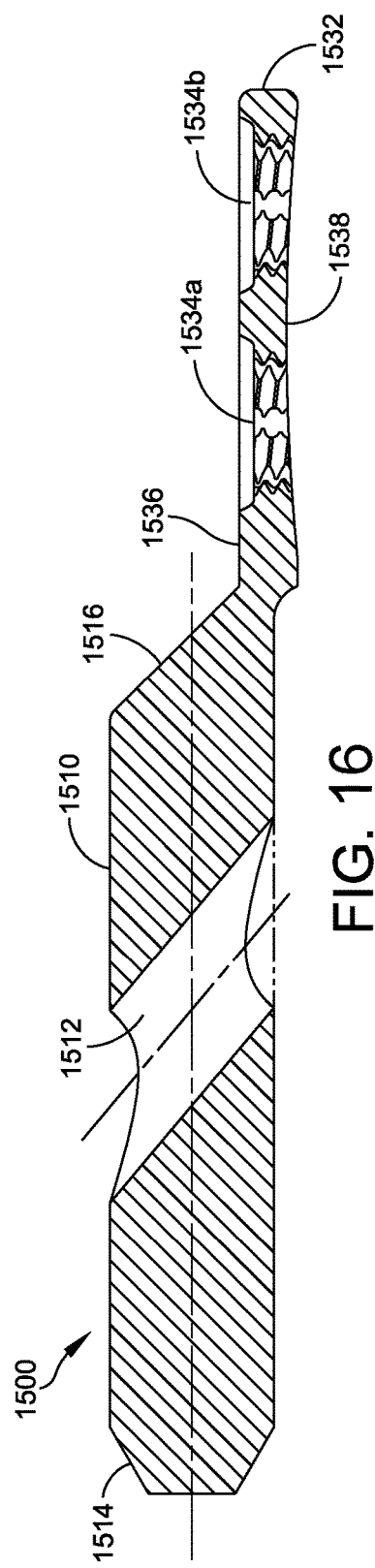

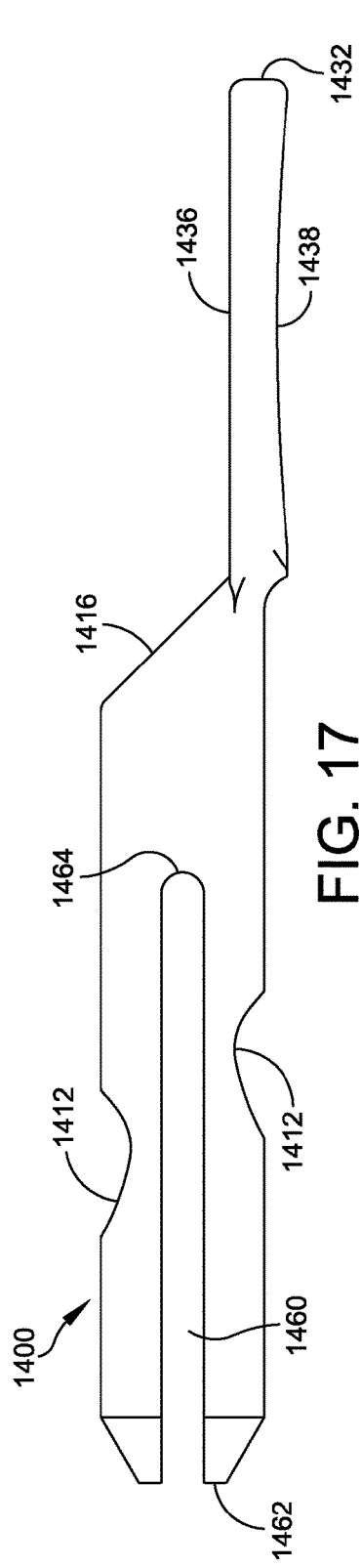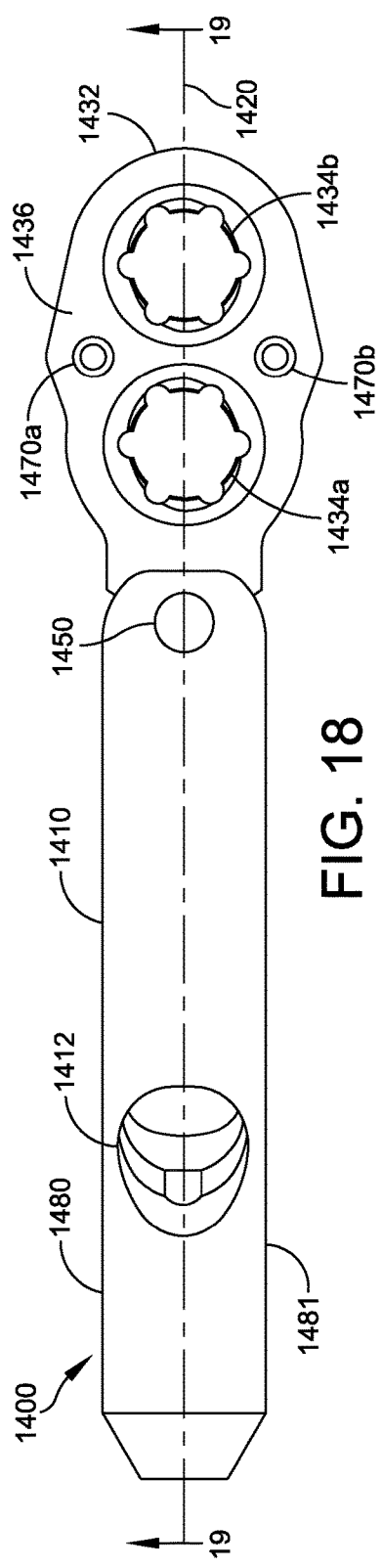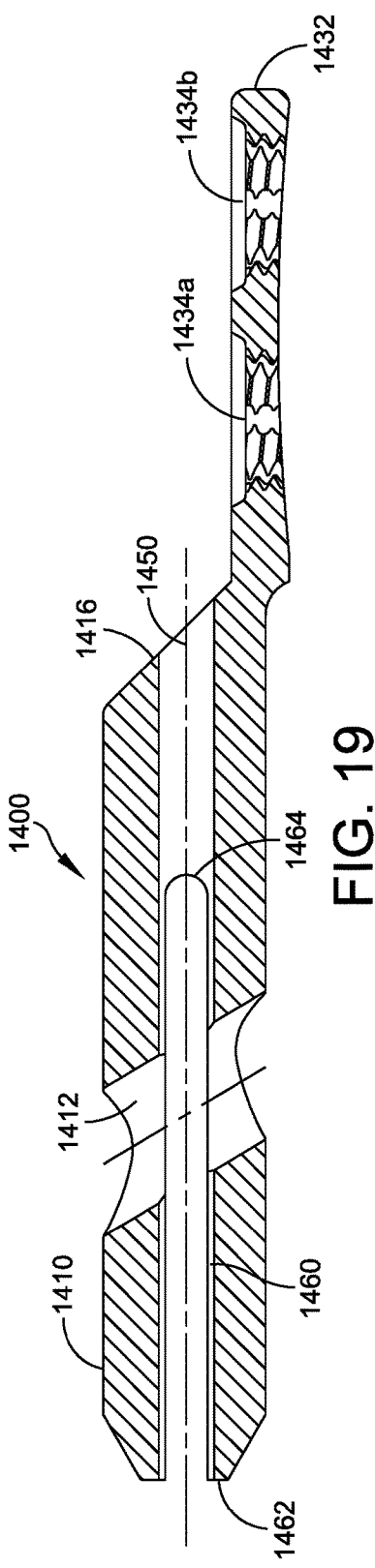

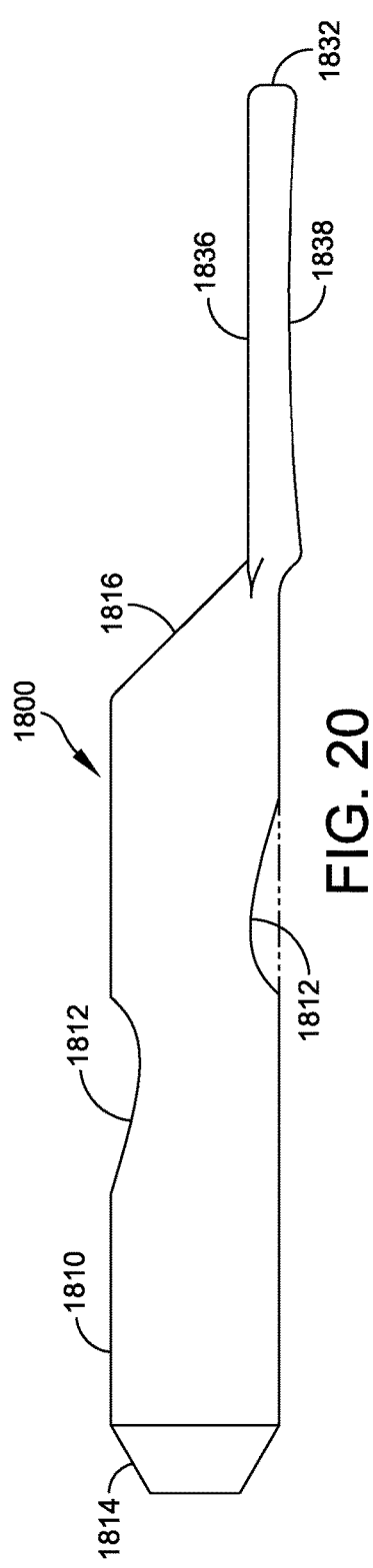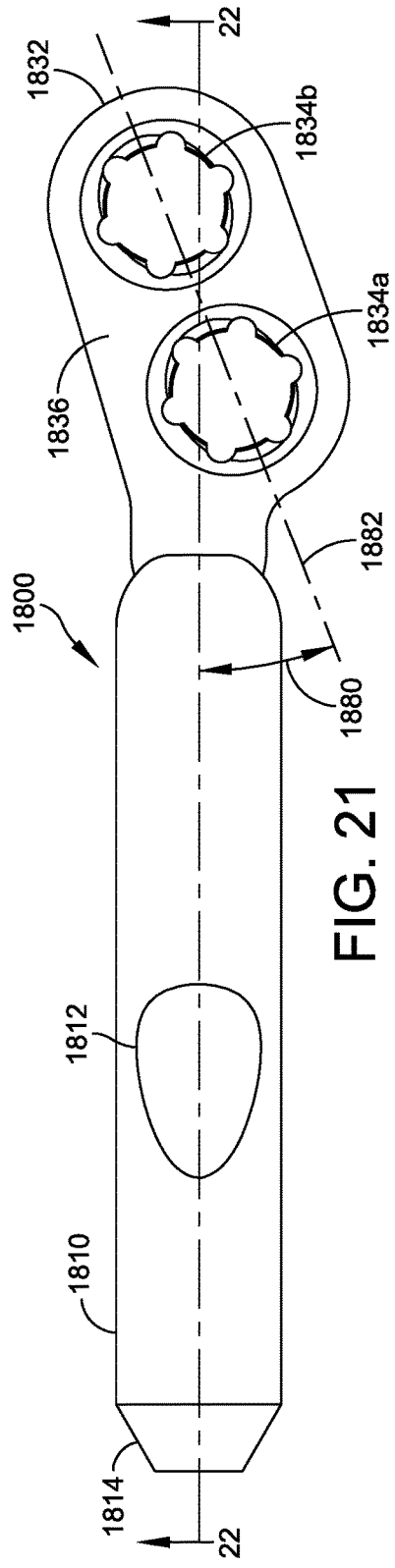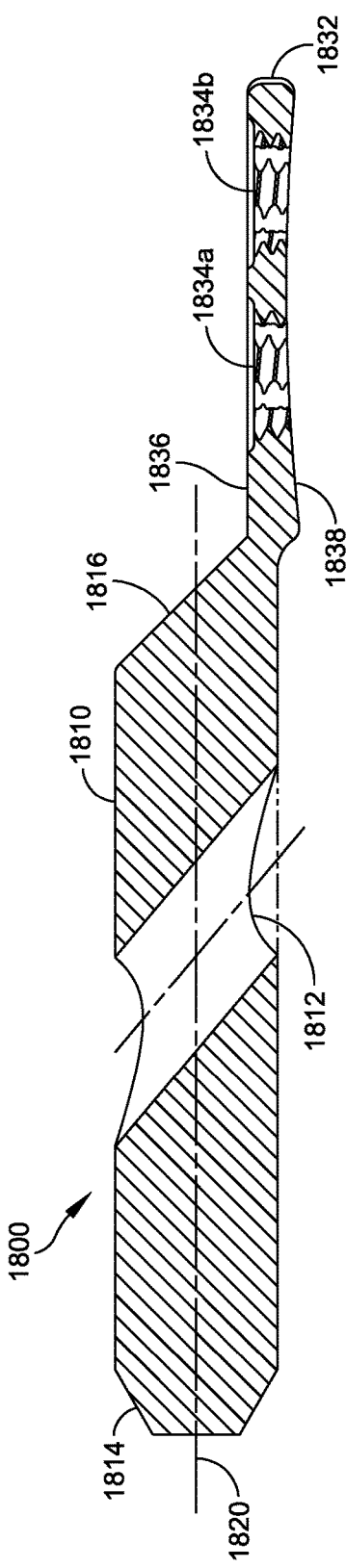

IMPLANT WITH INTRAMEDULLARY PORTION AND VARIABLE ANGLE EXTRAMEDULLARY PORTION

CROSS-REFERENCE TO RELATED APPLICATIONS

This application is a National Stage Application, filed under 35 U.S.C. 371, of International Patent Application No. PCT/US2020/050978, filed on Sep. 16, 2020, which claims priority to U.S. Provisional Patent Application No. 62/950,245, filed on Dec. 19, 2019, the entireties of which are incorporated herein by reference.

FIELD

This disclosure relates generally to medical devices, and more specifically to implants for correcting bone deformity.

BACKGROUND

Hallux valgus deformities in the human foot relate to a condition in which the first (great) toe has a deviated position leaning in towards the second toe. The first metatarsal deviates towards the mid-sagittal plane, and the great toe deviates away from the mid-sagittal plane. This is often accompanied by a bump due to a swollen bursal sac or a bony anomaly on the metatarsophalangeal joint.

A variety of non-surgical methods are used to treat hallux valgus, but in cases of continued pain or visible deformity, the patient may seek a surgical correction of the condition. Surgical methods may include removing the bony enlargement of the first metatarsal, realigning the first metatarsal bone relative to the adjacent metatarsal bone, and/or straightening the great toe relative to the first metatarsal and adjacent toes. Such surgical methods may result in visible scarring.

SUMMARY

In one aspect, an implant configured to attach a first bone section to a second bone section comprises an intramedullary portion and an extramedullary portion. The intramedullary portion is configured for insertion into the first bone section. The extramedullary portion is configured to abut a surface of the second bone section and includes a first fastener aperture configured to receive a bone fastener inserted in the second bone section. The intramedullary portion and the extramedullary portion are coupled such that the extramedullary portion is rotatable with respect to the intramedullary portion.

In another aspect, an implant system includes a nail, screw, k-wire, or rod and an implant configured to attach a first bone section to a second bone section. The implant includes an intramedullary portion and an extramedullary portion. The intramedullary portion is configured for insertion into the first bone section. The extramedullary portion is configured to abut a surface of the second bone section and includes a first fastener aperture configured to receive a bone fastener inserted in the second bone section. The intramedullary portion and the extramedullary portion are coupled such that the extramedullary portion is rotatable with respect to the intramedullary portion.

In another aspect, a method of treating a hallux valgus includes performing an osteotomy in a bone to separate a distal section of the bone from a proximal section of the bone. The method further includes forming a longitudinal hole in the proximal section of the bone. The method further includes inserting an intramedullary portion of an implant into the longitudinal hole, the implant having an extramedullary portion rotatably coupled to the intramedullary portion and the extramedullary portion has a first fastener aperture. The method further includes inserting a fastener through the first fastener aperture and into the distal section to attach the extramedullary portion to the distal section.

In another aspect, a target guide includes a threaded portion, a body, and an arm. The threaded portion is adapted to engage a first fastener aperture of an implant. The body is coupled to the threaded portion and is adapted to extend from a portion of the implant defining the first fastener aperture when the threaded portion engages the first fastener aperture. The arm is rotatably coupled to the body. The arm includes a guide aperture penetrating the arm and adapted for targeting a drill for drilling a hole through a second fastener aperture in an intramedullary portion of the implant.

BRIEF DESCRIPTION OF THE DRAWINGS

FIG. 1 is a lateral view of an exemplary implant according to one embodiment.

FIG. 2 is a superior view of the exemplary implant of FIG. 1.

FIG. 3 is a cross-sectional view taken along section line 3-3 of FIG. 1.

FIG. 5 is a medial view of the target guide of FIG. 4.

FIG. 6 is a lateral view of the target guide of FIG. 4.

FIG. 8 is an anterior view of the target guide viewed from line 8-8 of FIG. 4.

FIG. 9 is a posterior view of the target guide viewed from line 9-9 of FIG. 4.

FIG. 14 is a superior view of an exemplary implant according to one embodiment.

FIG. 15 is a lateral view of the exemplary implant of FIG. 14.

FIG. 16 is a cross-sectional view taken along section line 16-16 of FIG. 15.

FIG. 17 is a superior view of an exemplary implant according to another embodiment.

FIG. 18 is a lateral view of the exemplary implant of FIG. 17.

FIG. 19 is a cross-sectional view taken along section line 19-19 of FIG. 18.

FIG. 20 is a lateral view of an exemplary implant according to an additional embodiment.

FIG. 21 is a superior view of the exemplary implant of FIG. 20.

FIG. 22 is a cross-sectional view taken along section line 22-22 of FIG. 21.

DESCRIPTION

Figure 4:
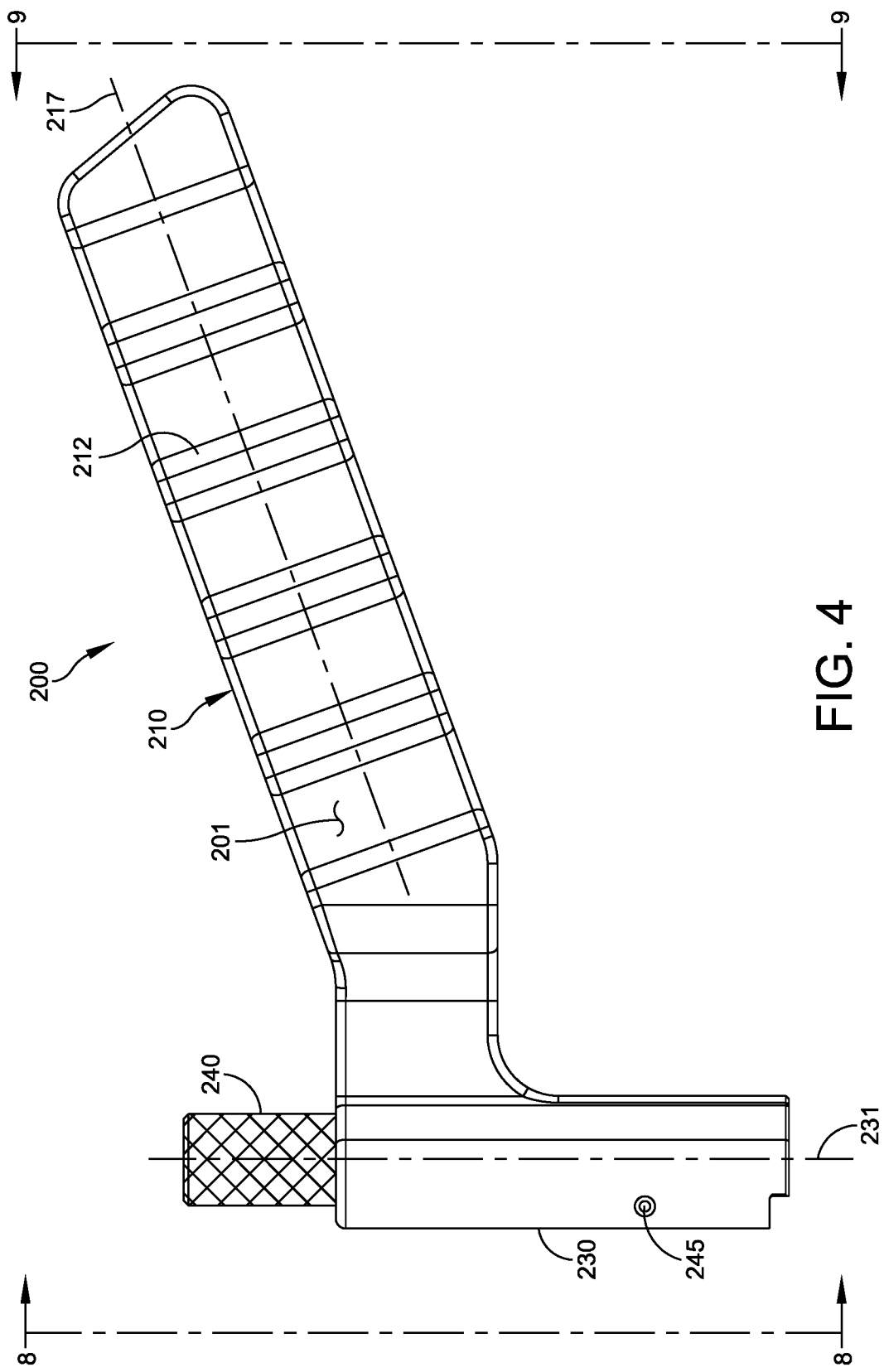
FIG. 4 is an inferior view of a target guide for use with the implant of FIG. 1.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. In the various drawings, like reference numerals indicate like items, unless expressly stated otherwise.

This disclosure provides an implant and a target guide for preparing the bones for the surgery, and a treatment method for inserting the implant suitable for minimally-invasive correction of hallux valgus (or of an analogous deformity in another joint). Although the drawings show application of the implant and target guide to treat a first metatarsal for correction of hallux valgus, the implant and target guide can be sized and configured to treat other bones, and can also be used in a variety of minimally-invasive or open procedures.

Figure 13:
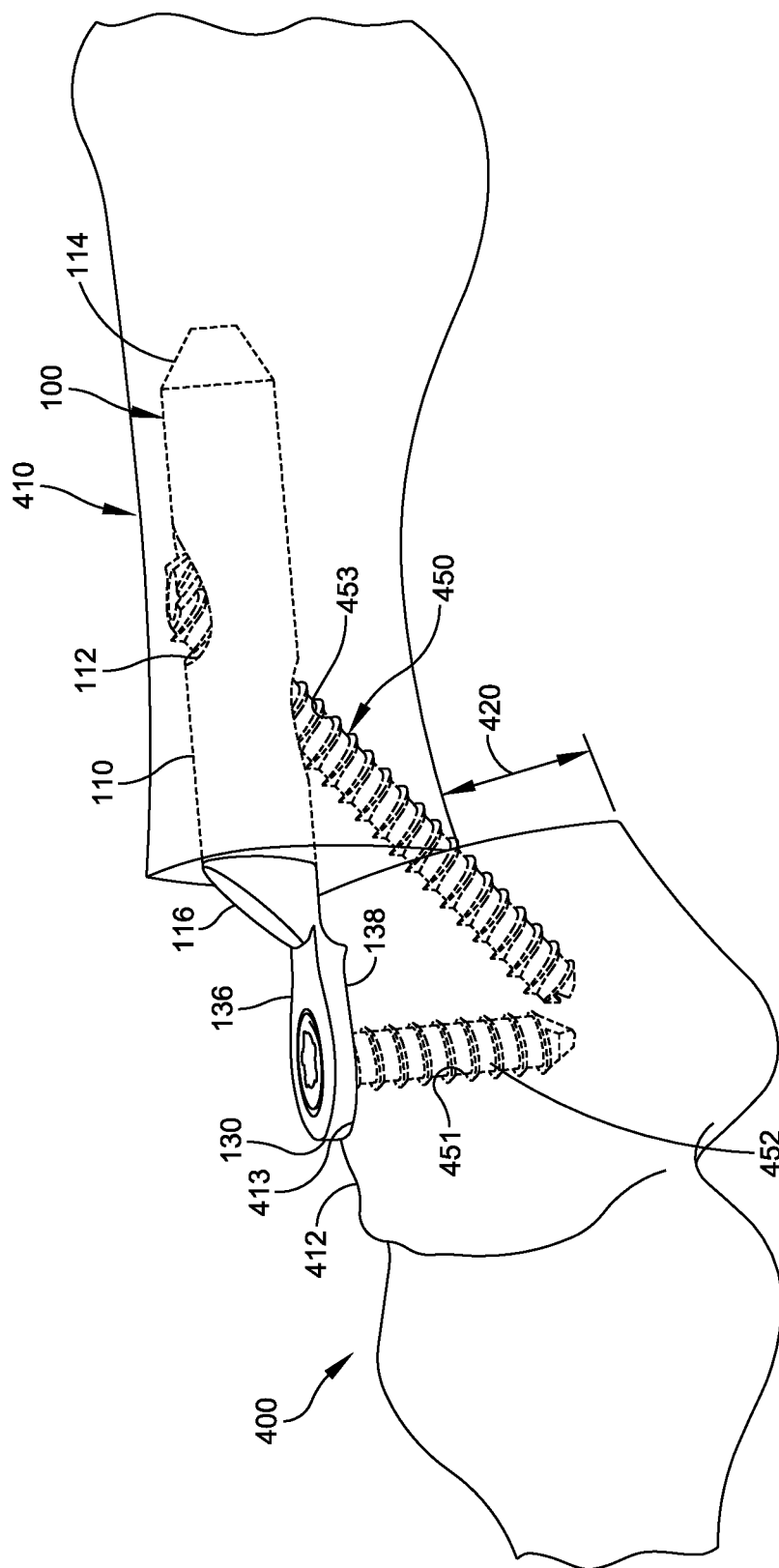
FIG. 13 shows the first metatarsal of FIG. 12B, after insertion of the implant.

FIGS. 1-3 show a first example of the implant 100. FIG. 1 is a plan view of the implant 100. FIG. 2 is a medial (or lateral) side view of the implant 100 of FIG. 1. FIG. 3 is a cross-sectional view of the implant 100 of FIG. 1, taken along section line 3-3. FIG. 13 shows the implant 100 in situ after insertion in the foot 400 of a patient.

Referring to FIGS. 1-3, the implant 100 has a unitary body including an intramedullary portion 110 connected to an extramedullary portion 130. The unitary body of implant 100 is configured to attach a first bone section 410 (FIG. 13) to a second bone section 412 (FIG. 13). It should be noted that the implant 100 can be used on either left or right foot.

The intramedullary portion 110 has a first longitudinal axis 120, which can be a central axis. The intramedullary portion 110 is configured for insertion into the first bone section 410 (FIG. 13). The intramedullary portion 110 includes at least one first fastener aperture 112 having an aperture axis 122. In some embodiments, the aperture axis 122 is oriented obliquely relative to the first longitudinal axis 120. In other embodiments (not shown), the aperture axis 122 is from about 90 degrees to about 180 degrees from the first longitudinal axis. For example, in some embodiments, the aperture axis 122 is oriented orthogonal to the first longitudinal axis 120. The at least one first fastener aperture 112 is configured to receive a nail, screw, k-wire or rod extending therethrough. In other embodiments (not shown), the at least one first aperture 112 is oriented along the first longitudinal axis 120 which may be distinct, and not parallel, to a second aperture and aperture axis 122. FIG. 13 shows a screw 450 in the first fastener aperture 112; a nail, k-wire or rod can be positioned in the same location in the first bone section 410, as shown in FIG. 13.

The extramedullary portion 130 is configured to abut a surface of the second bone section 412 (FIG. 13). The extramedullary portion 130 includes at least one second (distal) fastener aperture 134 disposed to receive a bone fastener 452 (e.g., an "Ortholoc® 3Di™" locking screw sold by Wright Medical Technology, Inc. of Memphis, TN), inserted in the second bone section 412. The bone fastener 452 may be disposed transversely or obliquely, relative to the fastener aperture 134. In some embodiments, polyaxial screws can be inserted with an angle of 0.0 to about 15 degrees from the transverse axis of the second (distal) fastener aperture 134. In some embodiments, polyaxial screws such as 3Di locking screws or non-locking screws sold by Wright Medical Technology, Inc. of Memphis, TN may be utilized. The extramedullary portion 130 has a second longitudinal axis 121 parallel to, and offset from, the first longitudinal axis 120.

The extramedullary portion 130 has a first side 136 facing radially inward (opposite the radial direction R) toward the first longitudinal axis 120 and a second side 138 facing radially outward (in the radial direction R) away from the first longitudinal axis 120. In some embodiments, the second side 138 has a concave surface adapted to engage a curved bone surface 413.

In some embodiments, the intramedullary portion 110 comprises a cylinder or cylindrical shaft having an outer surface 105, and the extramedullary portion 130 is joined to the intramedullary portion 110 so that a portion of the outer surface 105 is located between the first side 136 of the extramedullary portion 130 and the second side 138 of the extramedullary portion 130. That is, the first side 136 can be located radially inward from the surface 105, and the second side 138 can be located radially outward from the surface 105. The offset 123 between the first longitudinal axis 120 of the intramedullary portion 110 and the second longitudinal axis 121 of the extramedullary portion 130 can have a variety of values, each corresponding to a different amount of translation (also referred to as "shifting") of the first bone.

In some embodiments, the intramedullary portion 110 has a tapered proximal end 114. The tapered proximal end 114 facilitates insertion of the implant 100 into a longitudinal hole in the first (proximal) section 410 of the bone. The intramedullary portion 110 can also have a beveled distal end 116 to provide a smoother transition between the first bone section 410 (FIG. 13) and the second bone section 412 (FIG. 13).

The implant 100 can comprise a metal, such as titanium, stainless steel, or CoCr. In some embodiments, the implant 100 can comprise a metal substrate coated with or having an additional layer of hydroxyapatite (HA), titanium plasma spray (TPS)/vacuum plasma spray (VPS), roughened surface of resorbable blast media (RBM), a bioactive glass, an antimicrobial or antibiotic, or strontium. Alternatively, the implant 100 can comprise a metal substrate with a composite coating or composite layer including HA on plasma, beads, an irregular sintered coating or TPS on an RBM-prepared substrate. In other embodiments, the metal substrate can have a porous coating, such as spherical bead, asymmetrical powder or an irregular particle coating.

In some embodiments, the metal substrate of implant 100 comprises a degradable (resorbable) material, such as a magnesium alloy, which may contain lithium, aluminum, rare earth metals (e.g., neodymium or cerium), manganese, zinc or other metals. In other embodiments, the resorbable material can include, but are not limited to polymer materials including polyether ether ketone (PEEK), a polylactide, polyglycolide, polycaprolactone, polyvalerolactone, polycarbonates, polyhydroxy butyrates, poly ortho esters, polyurethanes, polyanhydrides, and combinations and copolymers thereof, for example.

In some embodiments, the implant 100 comprises a biologic material. The biologic material can be a combination of Medical grade β-TCP granules and rhPDGF-BB solution, such as "AUGMENT®" bone graft material sold by Wright Medical Technology, Inc. of Memphis, TN. The biologic material can be applied, sprayed, or inserted at the wound site for bone in-growth, or can be provided as a coating on the implants or any or all portions of the implant system. In some embodiments, the biologic material is a coating containing osteoinductive or osteoconductive biological components. In some embodiments, the biologic material can include bone morphogenetic factors, i.e., growth factors whose activity are specific to bone tissue including, but not limited to, demineralized bone matrix (DBM), bone protein (BP), bone morphogenetic protein (BMP), and mixtures and combinations thereof. Additionally, formulations for promoting the attachment of endogenous bone may comprise bone marrow aspirate, bone marrow concentrate, and mixtures and combinations thereof.

Figure 7:
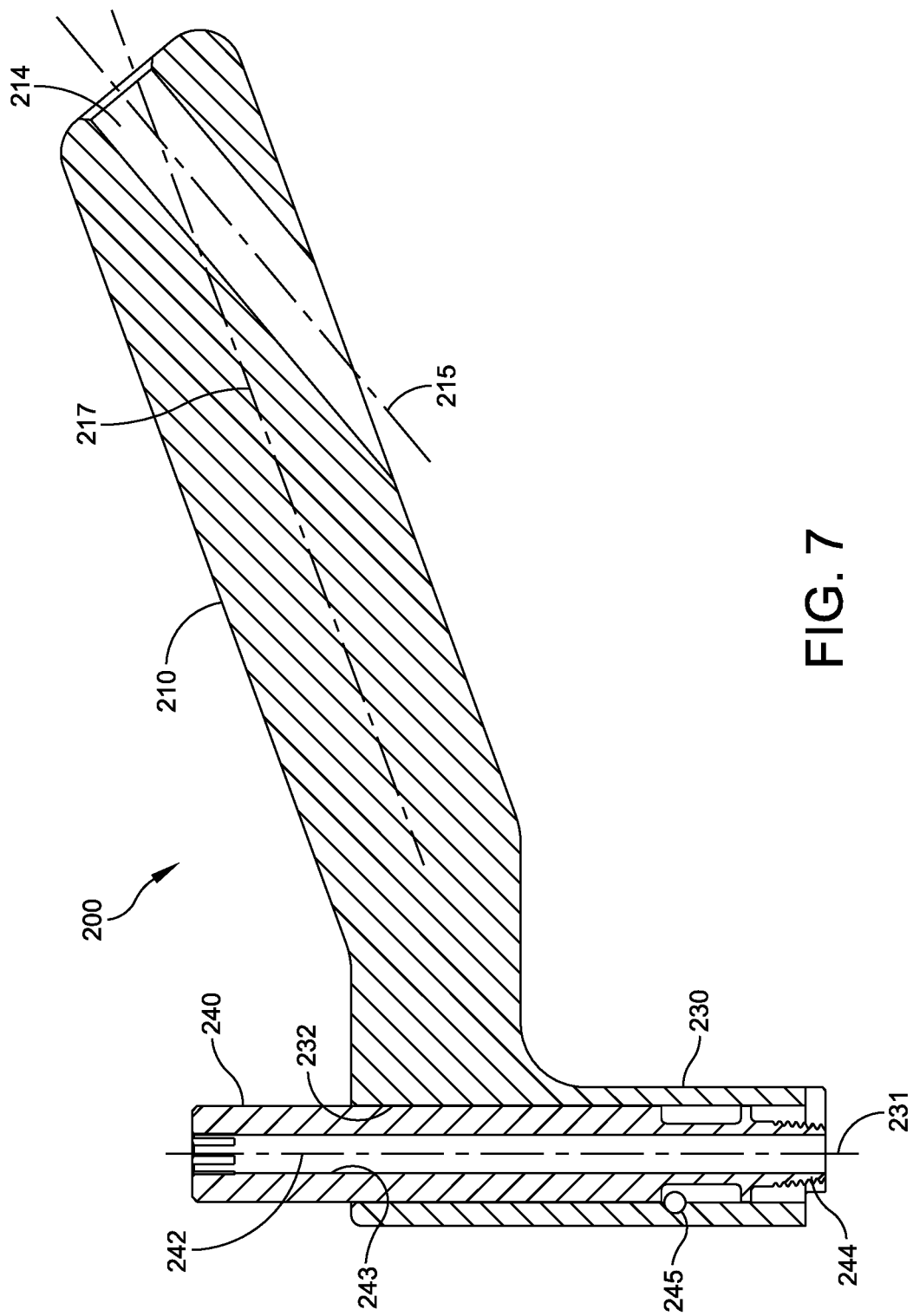
FIG. 7 is a cross-sectional view of the target guide taken along section line 7-7 of FIG. 5.
Figure 12A:
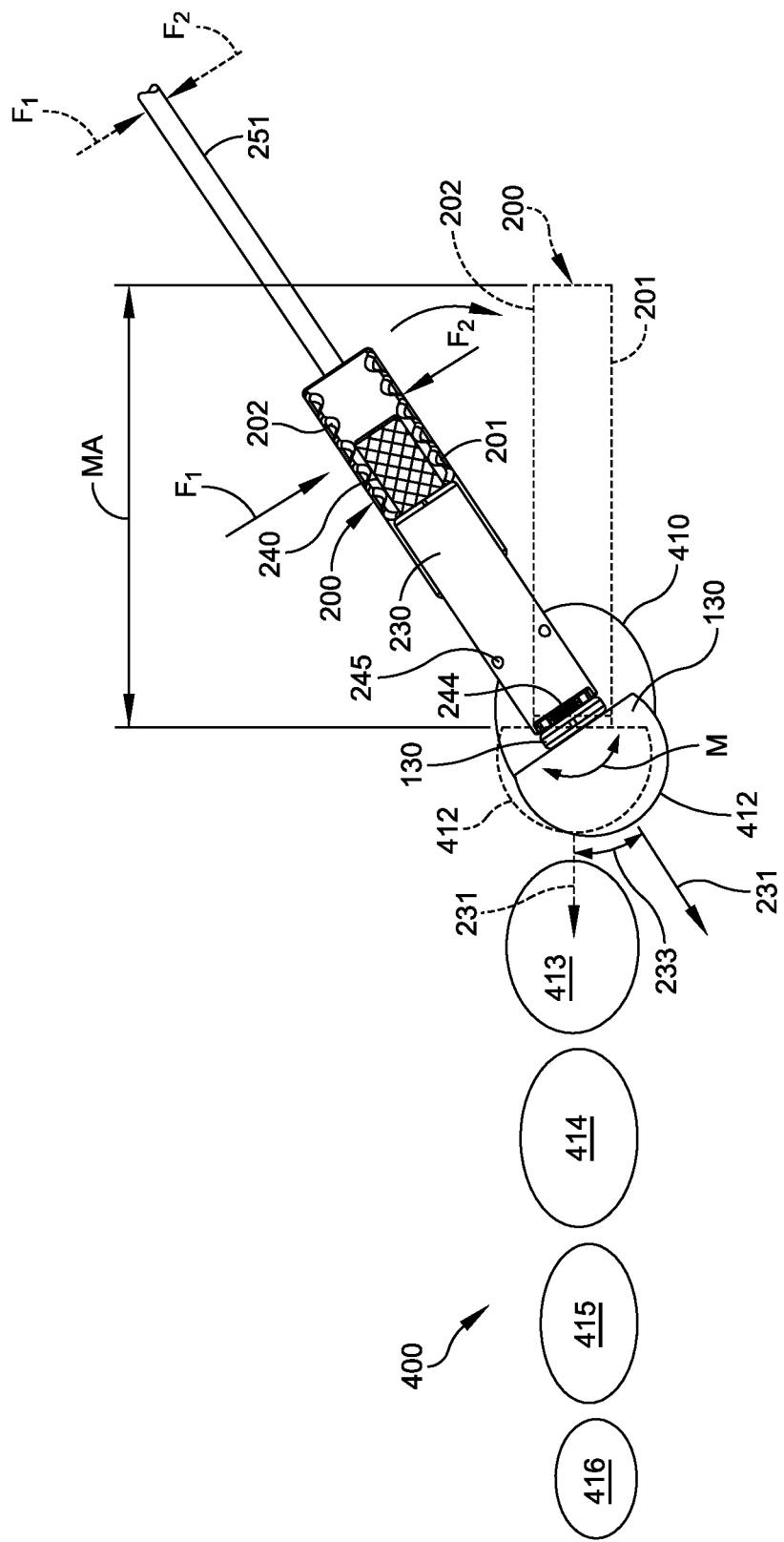
FIG. 12A is an anterior view of a foot, showing use of the target guide of FIG. 4 as a tool for positioning and rotating the implant of FIG. 1 and the distal section of a first metatarsal.
Figure 12B:
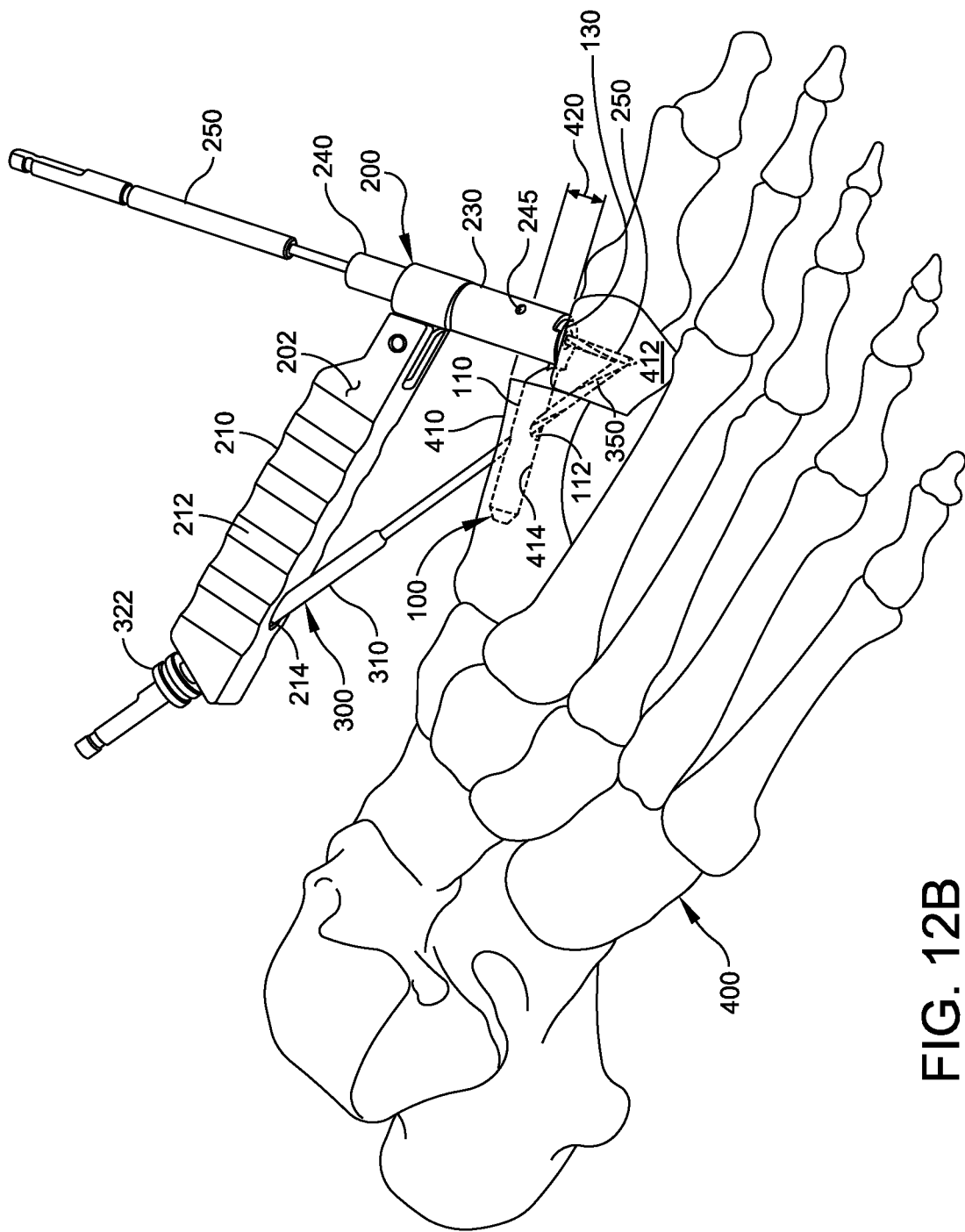
FIG. 12B shows the targeting guide in position for drilling a distal hole and an inter-fragment hole in the first metatarsal of the foot of FIG. 12A.

FIGS. 4-9 show a target guide 200 suitable for guiding drills to form fastener holes in a bone, for insertion of the implant 100 into the first bone section 410 (FIG. 13) and attachment of the second bone section 412 (FIG. 13). FIG. 4 is a plantar view of the target guide 200 (when used for treating the right foot as shown in FIG. 12B), and FIG. 12B shows the dorsal side of the target guide 200. FIG. 5 is a medial view of the target guide 200. FIG. 6 is a lateral view of the target guide 200. FIG. 7 is a cross-sectional view of the target guide 200 taken along section line 7-7 of FIG. 5. FIG. 8 is an anterior view of the target guide 200. FIG. 9 is a posterior view of the target guide 200.

A single target guide 200 can be used for treating hallux valgus in both right feet and left feet. FIGS. 12A-12B show the target guide 200 in use on a right foot 400, with the side 202 facing in the dorsal direction, and the side 201 facing in the plantar direction. When the target guide 200 is used for treating the left foot (not shown), the target guide 200 is flipped over, so that the side 201 of the target guide 200 shown in FIG. 4 becomes the dorsal side, and the side 202 shown in FIG. 12B becomes the plantar side. The medial, lateral, anterior, and posterior views correspond to FIGS. 5, 6, 8, and 9, respectively when treating the left foot (the same as when treating the right foot).

Referring again to FIGS. 4-9, the target guide 200 has a hollow cylinder 230, and a body 240 having threaded portion 244 attached thereto. The body 240 is disposed concentrically in the hollow cylinder 230. The body 240 has a central longitudinal passage 242 with a central longitudinal axis 231. The threaded portion 244 is adapted to engage a distal fastener aperture 134 of the implant 100. In some embodiments, the hollow cylinder 230 has a passage 232 and a body 240 in the shape of a collar mounted in the passage 232 of the hollow cylinder 230. The central longitudinal passage 242 is used for guiding a drill to form a distal hole in the distal section 412 of the bone. The body 240 includes the threaded portion 244 and has an inner cylindrical wall 243 defining the central longitudinal passage 242. The inner cylindrical wall 243 is concentric with the passage 232 of the hollow cylinder 230.

The body 240 is concentrically mounted within hollow cylinder 230. A press-fit pin 245 (FIG. 12A) keeps the body 240 in place, but body 240 is freely rotatable within hollow cylinder 230 and this allows the threaded end 244 of body 240 to thread into the distal fastener hole 134 within the extramedullary portion 130 of implant 100.

In some embodiments, the central longitudinal passage 242 is sized to receive a drill guide, such as a threaded drill guide (not shown). In other embodiments, the body 240 is itself configured to act as a drill guide, and includes a threaded end, adapted to thread into the distal aperture 134 of the extramedullary portion 130.

As discussed below in the description of FIG. 12A, the body 240 is adapted to extend away from the extramedullary portion 130 defining the distal fastener aperture 134 of the implant 100, when the threaded portion 244 of body 240 engages the distal fastener aperture 134. The target guide 200 is adapted to apply a moment M to rotate the implant 100 around the first longitudinal axis 120 of the implant 100 when a force $F_1$ or $F_2$ is applied to the hollow cylinder 230, body 240 (or a k-wire 251 or drill 250, FIG. 12B, extending through the body 240), where the force $F_1$ or $F_2$ is applied in a direction orthogonal to the first longitudinal axis 120 of the implant 100 and through the central longitudinal axis 231 of the body 240. The central longitudinal axis 231 of the body 240 is perpendicular to the first longitudinal axis 120 of the intramedullary portion 110, maximizing the length of the moment arm MA about axis 120 (FIG. 2) for an external force $F_1$ or $F_2$ applied to the hollow cylinder 230 or body 240. Washers or spacers (not shown) can be placed between the plate 130 and the translated bone segment 412 to increase the amount of translation.

Referring again to FIGS. 4-9, the target guide 200 further comprises an arm 210 extending from the hollow cylinder 230. The arm 210 has a guide aperture 214 penetrating the arm 210 and adapted for targeting a second drill 350 for drilling a second hole (inter-fragment hole) 453 (FIG. 13) through a proximal bone section 410 and into the distal bone section 412. In some embodiments, the guide aperture 214 is configured to receive the drill guide 300 of FIGS. 10 and 11, described below.

The body 240 has a first longitudinal axis 231, and the guide aperture 214 of the arm 210 of target guide 200 has a second longitudinal axis 215 (FIG. 7). As described herein, in use, the second longitudinal axis 215 is configured to be aligned with the aperture axis 122 of the implant 100. The arm 210 has a third longitudinal axis 217 (FIG. 4), such that a plane passes through the first longitudinal axis 231, second longitudinal axis 215, and third longitudinal axis 217. The distal fastener aperture 134 of the extramedullary portion 130 penetrates an interface surface 125 of the extramedullary portion 130 of the implant 100. When the threaded portion 244 of body 240 engages the distal fastener aperture 134 of the implant 100, the longitudinal axis 231 of the body 240 is normal to the interface surface 125. In other embodiments (not shown), the guide aperture 214 and second longitudinal axis 215 align to a first aperture axis 122 of the implant while concurrently a second guide aperture and second longitudinal axis align to a second aperture axis in the implant which may be distinct, and not parallel, to the first aperture axis 122.

Figure 10:
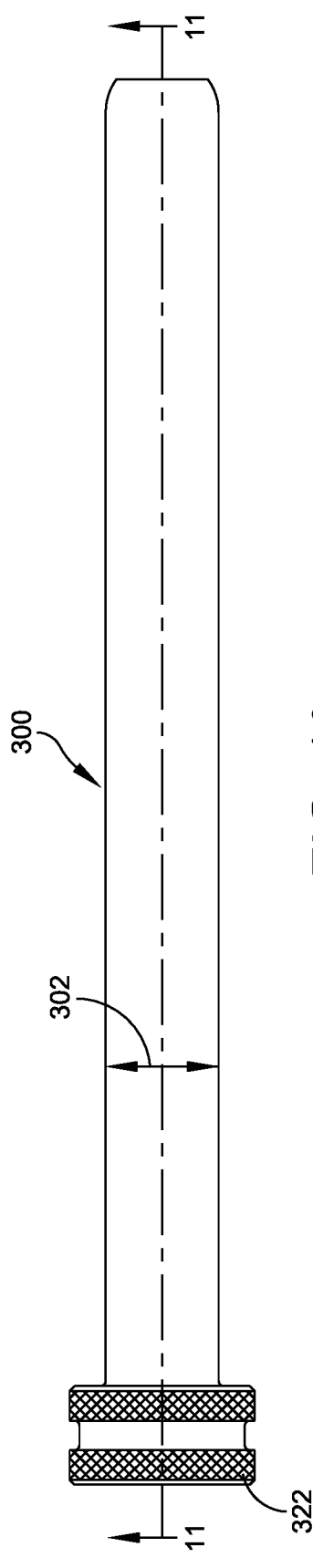
FIG. 10 is a side view of a drill guide configured for use with the target guide of FIG. 4.
Figure 11:
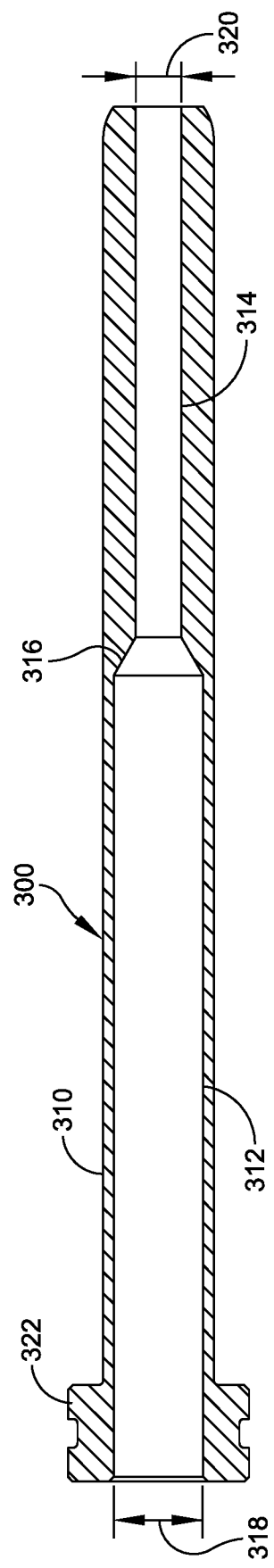
FIG. 11 is a cross-sectional view of the drill guide taken along section line 11-11 of FIG. 10.

FIGS. 10 and 11 show an example of a drill guide 300 suitable for use with the target guide 200. FIG. 10 is a plan view of the drill guide 300, and FIG. 11 is a cross-section of the drill guide 300, taken along section line 11-11 of FIG. 10. FIG. 12B shows the drill guide 300 in situ in the target guide 200.

In FIGS. 10 and 11, the drill guide 300 has an outer surface 310 with an outer diameter 302 sized to be slidably received in the guide aperture 214 of target guide 200. The drill guide 300 has a first portion with a bore 312 having a first inner diameter 318. The drill guide 300 has a second portion with a bore 314 having a second inner diameter 320 less than the first inner diameter 318. The second inner diameter 320 is sized to slidably receive and align a drill 350 (FIG. 12B) that penetrates the drill guide 300, the proximal bone section 410, the intramedullary portion 110 of the implant 100, and the distal bone section 412. The drill 350 forms an inter-fragment hole through the proximal bone section 410 and into the distal bone section 412. The first inner diameter 318 of the bore 312 of drill guide 300 is sized larger than the second inner diameter 320, to avoid friction between the drill 350 and the sidewall of bore 312. The drill guide 300 has a taper section 316 between (and connecting) the bore 312 and the bore 314, for guiding the drill 350 into the bore 314. The drill guide 300 may also have a knob 322 with a larger diameter than the outer surface 310. The knob 322 acts as a stop to prevent the drill guide 300 from falling out of the arm 210. The knob 322 can have a gripping surface, such as ridges, grooves, splines, or a knurled, patterned or textured surface.

FIG. 12A is an anterior view of a foot 400 having a first metatarsal, which has been separated into a proximal section 410 and a distal section 412. The foot 400 has second, third, fourth and fifth metatarsals, labeled 413, 414, 415 and 416, respectively. FIG. 12A shows the target guide 200 being used as a tool to position and rotate the implant 100 and the second (distal) section 412 of the bone (e.g., first metatarsal) about the first longitudinal axis 120 of implant 100 in situ, after the intramedullary portion 110 of implant 100 is inserted in a longitudinal intramedullary hole 414 (FIG. 12B) in the proximal section 410 of the bone. The distal section 412 and the target guide 200 are shown in solid lines to represent the position of the target guide 200 and distal section 412 before rotation. The distal section 412 and the target guide 200 are shown in phantom to represent the position of the target guide 200 and distal section 412 after rotation. The force $F_1$ or $F_2$ is shown as a solid line indicating application of the force $F_1$ or $F_2$ to directly to the body 240, and is shown in phantom to show the alternative position for application of the force $F_1$ or $F_2$ to the k-wire 251 or drill 250. The force $F_1$ can be applied in the clockwise direction, or the force $F_2$ can be applied in the counter-clockwise direction. The force F can be applied in the dorsal-plantar direction (as shown in FIG. 12A) or the plantar-dorsal direction (which would cause rotation in the opposite direction).

In some embodiments, the surgeon performs the osteotomy to separate the bone (e.g., first metatarsal) into a proximal section 410 and a distal section 412. The surgeon drives a k-wire (not shown) transversely into the distal section 412 of the bone. Then the surgeon passes the body 240 over the k-wire, so the k-wire penetrates through the central longitudinal passage 242 (of body 240), and the threaded portion 244 of the body 240 threadably engages the distal fastener opening 134 of the implant 100. The surgeon inserts a longitudinal k-wire (not shown) in the proximal section 410 of the bone and uses a cannulated reamer (not shown) to form the longitudinal intramedullary opening 414 (FIG. 12B) in the proximal section 410 concentric with the longitudinal k-wire. The surgeon removes the longitudinal k-wire from the longitudinal intramedullary opening 414 and inserts the intramedullary portion 110 of the implant 100 into the longitudinal intramedullary opening 414. The surgeon then applies the force $F_1$ or $F_2$ to cause the rotation through the angle 233 as shown in FIG. 12A.

During the rotation, the surgeon applies the force $F_1$ or $F_2$ to hollow cylinder 230, body 240 (or to drill 250 or k-wire 251), resulting in application of a moment M to rotate implant 100 and distal section 412 of the bone about the longitudinal axis 120 of the intramedullary portion 110 of implant 100. Although the surgeon can apply the force $F_1$ or $F_2$ directly to the body 240, in some instances the surgeon may wish to grasp the hollow cylinder 230, drill 250 or k-wire 251, and use the hollow cylinder 230, drill 250 or k-wire 251 as a joy stick during the rotation. The greater the moment arm MA, the smaller the force $F_1$ or $F_2$ can be, and vice-versa. The surgeon applies the force $F_1$ or $F_2$ to rotate implant 100 until the axis 231 of the body 240 rotates through a desired angle 233, so the extramedullary portion 130 of the implant 100 and distal bone section 412 are properly aligned with respect to the proximal section 410 of the bone. As shown in FIGS. 12A and 12B, when the extramedullary portion 130 is aligned with respect to the first bone section 410, the extramedullary portion 130 applies the desired correction (including rotation) to the second bone section 412.

The implant 100 can be provided with a variety of offsets 123 between the first longitudinal axis 120 of the intramedullary portion 110 and the second longitudinal axis 121 of the extramedullary portion 130. The offset 123 determines the translation applied to the second bone section 412 relative to the first bone section 410. The surgeon can select the implant 100 having an offset 123 that provides the desired translation.

FIG. 12B shows the target guide 200 after rotating the implant 100 and positioning the distal bone section 412. In FIG. 12B, the target guide 200 has a central longitudinal passage 242 (FIG. 11) penetrating the hollow cylinder 230. The central longitudinal passage 242 is adapted for targeting the first cannulated drill 250 for drilling a distal hole 451 (FIG. 13) in the distal bone section 412. The surgeon uses the drill guide 300 and a cannulated drill 350 to drill the inter-fragment hole 453 (FIG. 13). The inter-fragment hole 453 passes through the proximal section 410 of the bone and into the distal section 412 of the bone. Thus, a single target guide 200 can be used as a tool for positioning and rotating the implant 100 and distal section 412 relative to the proximal section 410, and as a guide for drilling the distal hole 451 and the inter-fragment hole 453 to receive bone fasteners to maintain the correct positions and alignment of the distal section 412.

The target guide described above is only exemplary and is not limiting. For example, in a variation of the target guide (not shown), the body 240 is not pre-assembled within the hollow cylinder 230, and the press-fit pin 245 is omitted. The surgeon or technician can assemble the body 240 (or a drill guide, not shown, having the same outer diameter as body 240) inside the hollow cylinder 230 before use. With a removable body 240 or drill guide, the surgeon can remove the body 240 or drill guide and implant the distal fastener 452 (FIG. 13) through the hollow cylinder 230 of the target guide 200, without first removing the target guide 200. This provides greater flexibility in surgical technique and procedures.

Figure 12C:
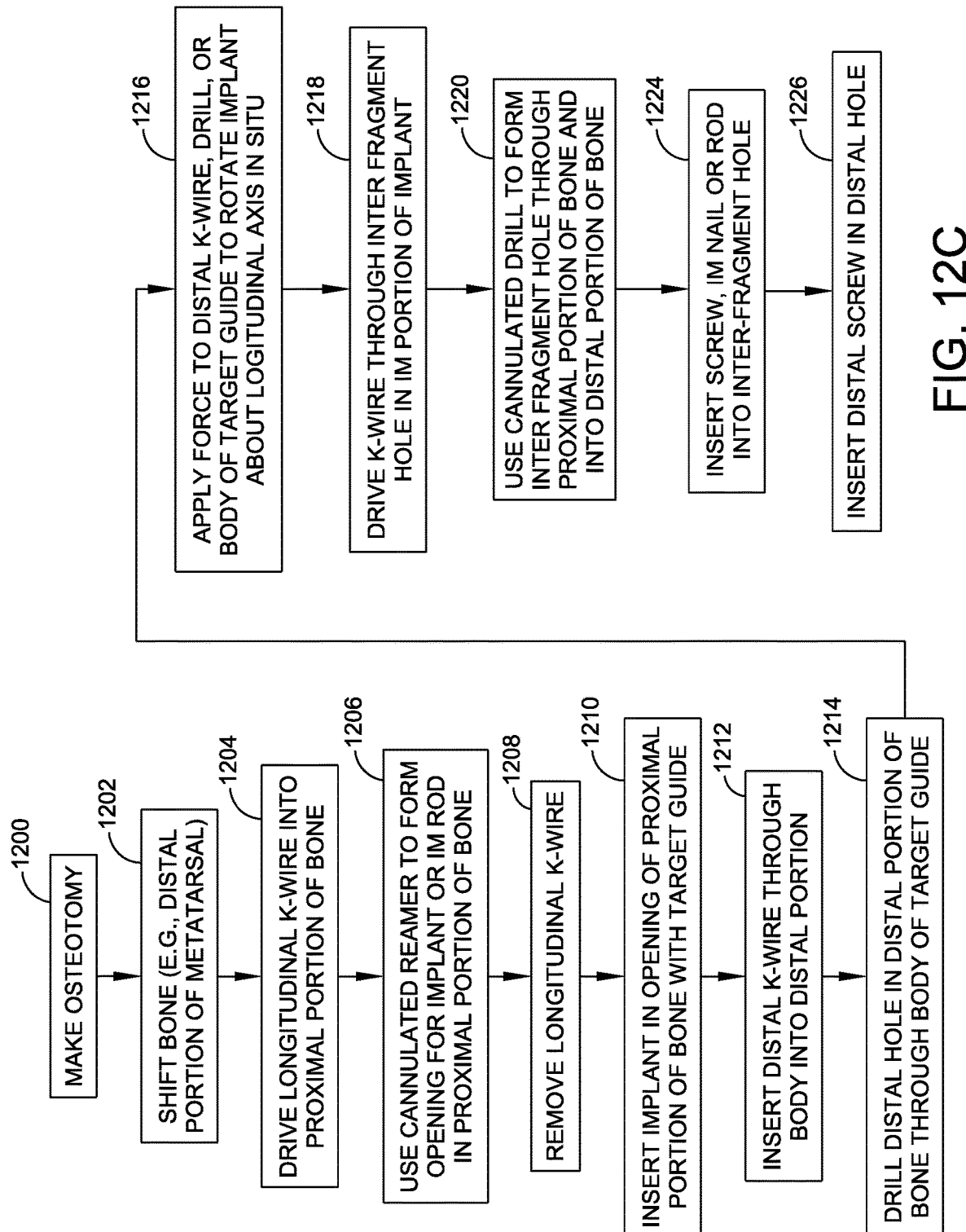
FIG. 12C is a flow chart of a method of treatment using the implant of FIG. 1 and the target guide of FIG. 4.

FIG. 12C is a flow chart showing an example of a method for using the target guide.

At step 1200, the surgeon performs an osteotomy to separate a bone into proximal and distal sections. For example, the surgeon can perform a transverse osteotomy to separate a first metatarsal into a proximal section and a distal section. (The remainder of the description of FIG. 12C refers to the bone as the first metatarsal of a foot, but this is a non-limiting example, and the method can be applied to other bones.)

At step 1202, the surgeon shifts one of the bone portions, so a nearest medial edge of the distal section is offset from the first longitudinal axis. For example, the surgeon can move the distal section of the first metatarsal in the lateral direction to expose at least a portion of the cut (anterior) surface of the proximal section of the first metatarsal.

At step 1204, the surgeon drives a k-wire in the longitudinal direction (referred to herein as the longitudinal k-wire) into the cut surface of the proximal section of the first metatarsal.

At step 1206, the surgeon uses a cannulated reamer to form the longitudinal hole (for receiving the intramedullary portion of the implant), while the k-wire is in the proximal section.

At step 1208, the surgeon removes the longitudinal k-wire from the longitudinal intramedullary opening.

At step 1210, the surgeon attaches the target guide to the distal fastener opening in the extramedullary portion of the implant (by engaging the threaded end of the body of the target guide with the threads of the distal fastener opening). Alternatively, the surgeon can obtain a pre-packaged or previously assembled construct comprising an implant attached to the threaded end of the body of a target guide. The surgeon inserts the intramedullary portion of the implant into the longitudinal intramedullary opening in the proximal section of the first metatarsal. During the insertion, the surgeon may grip the body of the target guide to push the implant into the opening. When the insertion is completed, the extramedullary portion of the implant has a first side facing radially inward toward the first longitudinal axis of the implant and a second side facing radially outward from the first longitudinal axis, where the second side has a concave surface that abuts a curved bone surface of the distal section of the first metatarsal.

At step 1212, in some embodiments, the surgeon inserts a k-wire through the body of the target guide and drills the distal hole in the distal section of the first metatarsal. In other embodiments, the surgeon omits step 1212.

At step 1214, the surgeon inserts a cannulated drill through the body of the target guide and drills the distal hole in the distal section of the first metatarsal, while the k-wire still is place.

At step 1216, after inserting the intramedullary portion into the longitudinal hole, the surgeon applies a force to the target guide, a drill, or a k-wire to rotate the implant and the distal section of the first metatarsal about the first longitudinal axis in situ. The surgeon may handle the drill or k-wire like a joy stick to manipulate and rotate the implant and distal section of the first metatarsal. The surgeon uses the drill or k-wire that defines the trajectory of the distal fastener as a 'joystick' to find the optimum rotation angle (based on the location of the sesamoid bones of the first metatarsal, which the surgeon can identify through fluoroscope, and to provide additional correction of the intramedullary angle, IMA).

At step 1218, after applying the force to rotate the implant, the surgeon drives an inter-fragment k-wire through the target guide, the proximal section of the first metatarsal, a first aperture in the intramedullary portion of the implant and into distal section of the first metatarsal.

At step 1220, the surgeon uses a cannulated drill to form the inter-fragment hole while the k-wire is in the distal section. The surgeon drills through the proximal section of the first metatarsal and the first aperture of the implant, and into the distal section.

At step 1224, after forming the inter-fragment hole, the inter-fragment k-wire is removed from the inter-fragment hole, and the surgeon inserts a nail, screw, k-wire or rod through the proximal section of the first metatarsal and the first aperture, and into the inter-fragment hole. In some embodiments, the inter-fragment nail, screw, k-wire or rod has a cannula, and the inserting step comprises inserting the inter-fragment nail, screw, k-wire or rod in the inter-fragment hole with the k-wire extending through the cannula of the inter-fragment nail, screw, k-wire or rod.

At step 1226, the surgeon removes the distal k-wire from the distal hole, and then inserts the distal fastener (not shown in FIG. 12A) through the distal fastener aperture 134 and into the distal section 412. A distal fastener (such as a locking or non-locking screw) is inserted through the distal aperture and into the distal section of the first metatarsal, to attach the extramedullary portion of the implant to the distal section of the first metatarsal with a nearest medial edge of the distal section offset from the first longitudinal axis.

FIG. 13 shows the first metatarsal after completing the procedure shown in FIG. 12C. The implant system comprises the implant 100 and two or more bone fasteners 450, 452 selected from nails, screws, k-wires, rods or combinations thereof. The implant 100 has a unitary body including the intramedullary portion 110 connected to the extramedullary portion 130. The unitary body is configured to attach a first bone section 110 to a second bone section 112. The intramedullary portion 110 has a first longitudinal axis 120, and is configured for insertion into the first bone section 110. The intramedullary portion 110 includes at least one first fastener aperture 112 having an aperture axis 122 oriented obliquely relative to the first longitudinal axis 120 and adapted to receive the nail, screw, k-wire or rod 450. The extramedullary portion 130 is configured to abut a surface of the second bone section 412 and includes at least one second (distal) fastener aperture 134 disposed to transversely receive a bone fastener 452 inserted in the second bone section 412. The extramedullary portion 130 has a second longitudinal axis 121 parallel to, and offset from, the first longitudinal axis 120. Thus, the first longitudinal axis and a line between the respective centers of the two second fastener apertures 112, 134 form an oblique angle.

The bone fasteners 450, 452 can include two or more nails, screws, k-wires or rods or combinations thereof. For example, the bone fasteners 450, 452 can be selected from a cannulated screw, a lag screw, a compression screw, a locking screw, or a non-locking screw.

FIGS. 14-16 show an embodiment of an implant 1500 having two distal fastener apertures 1534*a*, 1534*b* to provide greater stability for the bone. The addition of a second distal screw offers an additional point of fixation for severe hallux valgus or in the case of poor bone quality. In the case where the implant 1500 is substituted for implant 100 in the FIG. 13, the second distal bone fastener prevents rotation of the distal section 412 of the first metatarsal in a sagittal plane (i.e., the implant 1500 prevents pitch motion).

The intramedullary portion 1510, second aperture 1512, taper 1514, and bevel 1516 can be the same as the respective intramedullary portion 110, second aperture 112, taper 114, and bevel 116 shown in FIGS. 1-3, and for brevity, descriptions of these items are not repeated. The extramedullary portion 1532 has a top surface 1536 and a bottom surface 1538, which are analogous to the extramedullary portion 130, top surface 136 and bottom surface 138 in FIGS. 1-3. However, extramedullary portion 1532 has two distal apertures 1534*a* and 1534*b*. The two distal apertures 1534*a* and 1534*b* are aligned with each other and positioned on the axis of symmetry of the implant 1500. The axis of symmetry appears in FIG. 15 and coincides with section line 16-16.

The implants are not limited to one distal fastener 134 (as shown in FIGS. 1-3) or two distal fasteners 1534*a*, 1534*b* (as shown in FIGS. 14-16). Other embodiments (not shown) can have more than two distal fasteners.

FIGS. 17-19 show another embodiment of the implant 1400 having two distal fastener apertures 1434*a*, 1434*b* to provide greater stability for the bone. Like the implant 1500 of FIGS. 14-16, the implant 1400 has two distal bone fasteners 1434*a*, 1434*b* to prevent rotation of the distal section 412 of the first metatarsal in the sagittal plane.

The intramedullary portion 1410, second aperture 1412, taper 1414, bevel 1416, extramedullary portion 1432 fastener apertures 1434*a*, 1434*b*, top surface 1436 and bottom surface 1438 of FIGS. 17-19 can be the same as the respective intramedullary portion 1510, second aperture 1512, taper 1514, bevel 1516, extramedullary portion 1532 fastener apertures 1534*a*, 1534*b*, top surface 1536 and bottom surface 1538, shown in FIGS. 14-16, and for brevity, descriptions of these items are not repeated.

However, in the example of FIGS. 17-19, the intramedullary portion 1410 has a cannula 1450 extending from the bevel 1416 to the proximal end 1462 of the implant 1400. The cannula 1450 allows insertion of the longitudinal k-wire through the central longitudinal axis 1420 of the implant 1400, so the implant 1400 is guided into place by the k-wire.

Implant 1400 also has a longitudinal slot 1460 passing through the central axis 1420 of the intramedullary portion 1410. The slot 1460 can extend from the proximal end 1462 (opposite from the extramedullary portion 1432) of the implant 1400, at least as far as the at least one first fastener aperture 1412. For example, in some embodiments, the slot 1460 extends from the proximal end 1462 to a termination 1464, where the termination 1464 is between the second aperture 1412 and the bevel 1416. The slot 1460 provides compression within the intramedullary canal, to help stabilize the intramedullary portion 1410. In some embodiments, the slot 1460 contains a biologic material. In some embodiments, the biologic material can be a combination of Medical grade β-TCP granules and rhPDGF-BB solution, such as "AUGMENT®" bone graft material sold by Wright Medical Technology, Inc. of Memphis, TN. In some embodiments, the biologic material can be a coating containing osteoinductive or osteoconductive biological components. The biologic material can include bone morphogenetic factors, i.e., growth factors whose activity are specific to bone tissue including, but not limited to, demineralized bone matrix (DBM), bone protein (BP), bone morphogenetic protein (BMP), and mixtures and combinations thereof. The slot 1460 also allows ingrowth of bone from dorsal and plantar directions. Additionally, formulations for promoting the attachment of endogenous bone may comprise bone marrow aspirate, bone marrow concentrate, and mixtures and combinations thereof.

In some embodiments, the longitudinal slot 1460 completely penetrates the intramedullary portion 1410, from the plantar side 1480 to the dorsal side 1481. The slot 1460 divides the cross section of the intramedullary portion 1410 into two approximately semicircular portions.

Also, extramedullary portion 1432 has two alignment apertures 1470*a*, 1470*b*, which are separate from the fastener apertures 1434*a*, 1434*b*, and into which pins or wires can be placed. The two distal apertures 1534*a* and 1534*b* are aligned with each other and positioned on the axis of symmetry of the implant 1500. The axis of symmetry appears in FIG. 15 and coincides with section line 16-16.

Although the implant 1400 includes the cannula 1450, the slot 1460 and the alignment apertures 1470*a*, 1470*b*, other embodiments may include any one, any two, or all three of these features.

FIGS. 20-22 show another embodiment of the implant 1800 having offset distal fastener apertures 1834*a*, 1834*b*. Like the implant 1500 of FIGS. 14-16, the implant 1800 has two distal bone fasteners 1834a, 1834b to prevent rotation of the distal section 412 of the first metatarsal in the sagittal plane.

The intramedullary portion 1810, second aperture 1812, taper 1814, and bevel 1816 of FIGS. 20-22 can be the same as the respective intramedullary portion 1510, second aperture 1512, taper 1514, and bevel 1516 of FIGS. 14-16, and for brevity, descriptions of these items are not repeated. The extramedullary portion 1832, fastener apertures 1834a, 1834b, top surface 1836 and bottom surface 1838 of implant 1800 are analogous to the corresponding extramedullary portion 1532, fastener apertures 1534a, 1534b, top surface 1536 and bottom surface 1538, shown in FIGS. 14-16.

However, at least one of the two second fastener apertures 1834a, 1834b has a center that is offset from the central longitudinal axis 1820 (which lies along the section line 22-22 and is shown in FIG. 22. For example, in FIG. 21, the implant 1800 has two distal fastener apertures 1834a and 1834b, both of which are offset from the central longitudinal axis 1820. In some embodiments, the centers of fastener apertures 1834a and 1834b both have the same distance from the central longitudinal axis 1820, but are arranged on opposite sides of the central longitudinal axis 1820. A line 1882 connecting the centers of fastener apertures 1834a and 1834b forms an angle 1880 with the central longitudinal axis 1820. In various embodiments, the angle 1882 can be varied to accommodate different shapes and positions of the distal section 412 of the first metatarsal. The offset configuration also allows the surgeon to position the fastener apertures 1834a and 1834b adjacent to the regions of the distal section 412 having the best bone quality.

In other embodiments, the number of distal fastener apertures and their positions can be varied.

Figure 23:
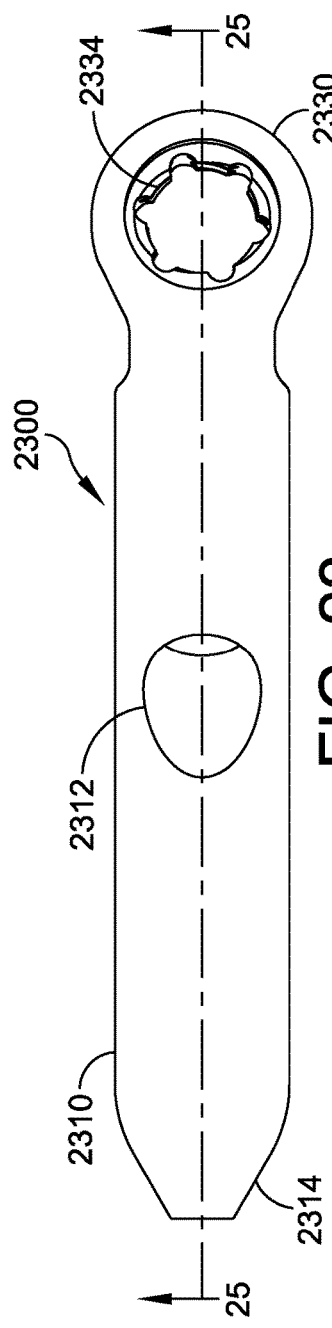
FIG. 23 is a lateral view of an exemplary implant according to another embodiment.
Figure 24:
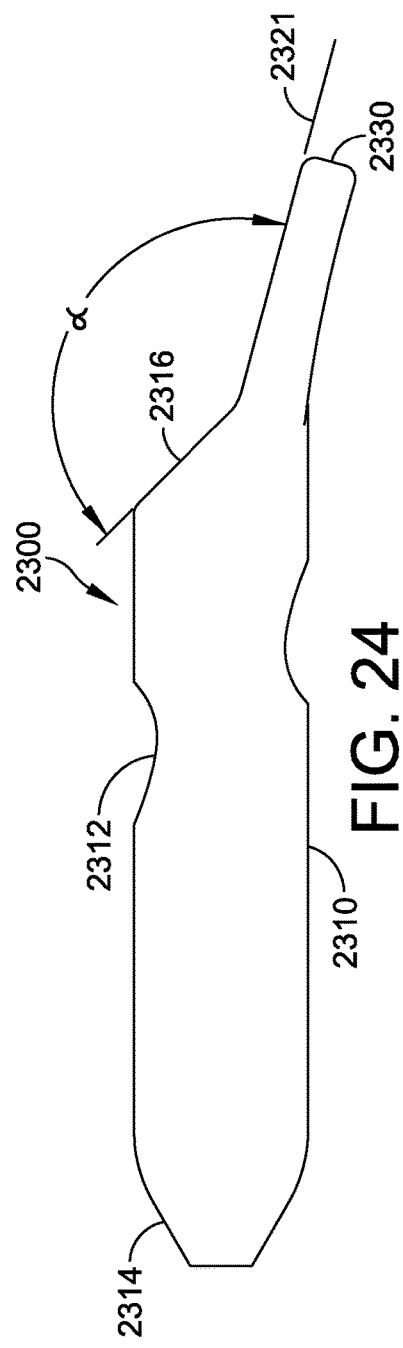
FIG. 24 is a superior view of the exemplary implant of FIG. 23.
Figure 25:
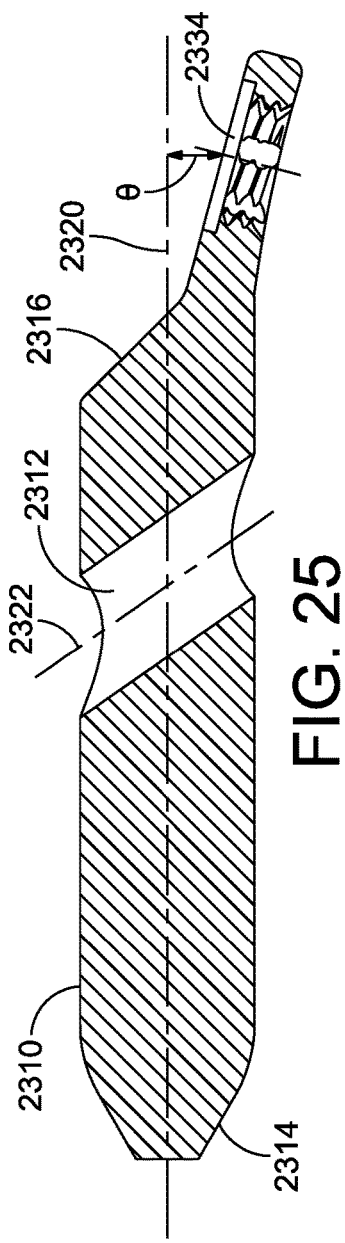
FIG. 25 is a cross-sectional view taken along section line 25-25 of FIG. 23.
Figure 30:
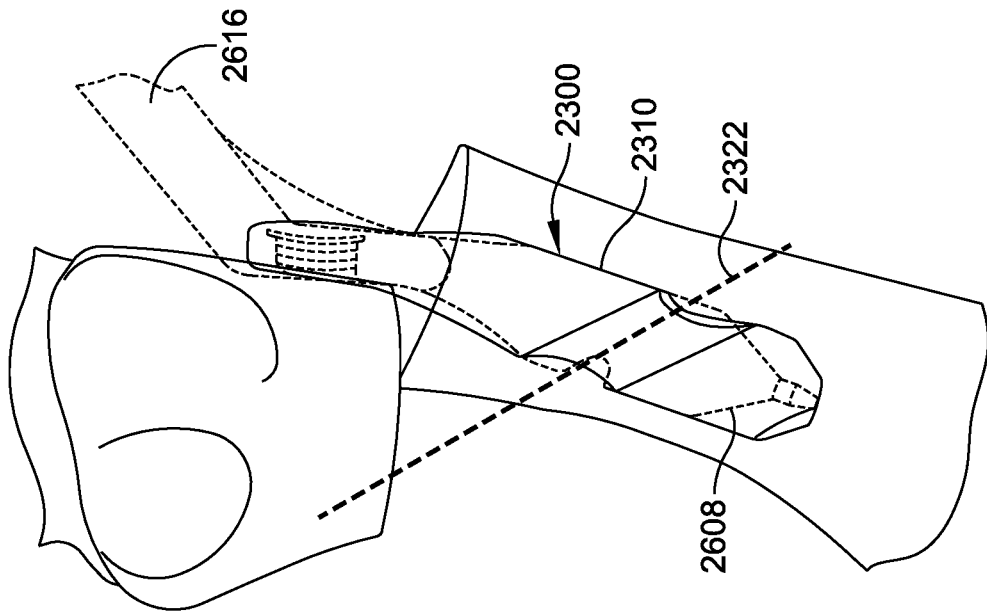
FIG. 30 is a schematic view of the implant of FIG. 23 superimposed on the broach of FIG. 29 in situ.

FIGS. 23-25 show another example of the implant 2300. The implant 2300 is configured to impart a lateral angular correction, to correct a medial deviation of the distal portion of the bone (e.g., metatarsal). Like the implant 100 of FIG. 1, implant 2300 includes an extramedullary portion 2330 that is offset from the central longitudinal axis of the intramedullary portion. Additionally, the extramedullary portion 2330 has an offset angle Θ (relative to the central longitudinal axis 2320 of the intramedullary portion 2310), shown in FIG. 25, for making the lateral angular correction. FIG. 23 is a lateral view of the implant 2300. FIG. 24 is a superior view of the implant 2300 of FIG. 23. FIG. 25 is a cross-sectional view of the implant 2300 of FIG. 23, taken along section line 25-25. FIG. 30 is a schematic diagram showing the implant 2300 in situ after insertion in the foot 400 of a patient—FIG. 30 also shows the broach 2600 (in phantom), superimposed on the implant 2300; the broach 2600 is used to form the intramedullary opening to receive implant 2300.

Referring to FIGS. 23-25, the implant 2300 has a unitary body including an intramedullary portion 2310 connected to an extramedullary portion 2330. The unitary body of implant 2300 is configured to attach a first bone section 410 (FIG. 13) to a second bone section 412 (FIG. 13).

The intramedullary portion 2310 can have the same size and shape as the intramedullary portion 110 of the implant 100 of FIG. 1. The intramedullary portion 2310 has a first longitudinal axis 2320, which can be a central axis. The intramedullary portion 2310 is configured for insertion into the first bone section 410 (FIG. 30). The intramedullary portion 2310 includes at least one first fastener aperture 2312 having an aperture axis 2322. The aperture axis 2322 is oriented obliquely relative to the first longitudinal axis 2320 and is configured to be co-axial to drill guide 300 when the drill guide 300 is inserted into the guide aperture 214 of the target guide 200. For example, the aperture axis 2322 can be 45 degrees from the first longitudinal axis 2320. The at least one first fastener aperture 2312 is configured to receive a screw, k-wire or rod extending therethrough.

In some embodiments, the intramedullary portion 2310 has a tapered proximal end 2314. The tapered proximal end 2314 facilitates insertion of the implant 2300 into a longitudinal hole in the first (proximal) section 410 of the bone. The intramedullary portion 2310 can also have a beveled distal end 2316 to provide a smoother transition between the first bone section 410 (FIG. 13) and the second bone section 412 (FIG. 13).

The extramedullary portion 2330 is configured to abut a surface of the second bone section 412 (FIG. 13). The extramedullary portion 2330 includes at least one second (distal) fastener aperture 2334 disposed to receive a bone fastener 452 inserted in the second bone section 412. The bone fastener 452 may be disposed transversely or obliquely, relative to the fastener aperture 2334. In some embodiments, polyaxial screws can be inserted with an angle of 0.0 to about 15 degrees from the transverse axis of the second (distal) fastener aperture 2334. The extramedullary portion 2330 has a second longitudinal axis 2321. The second longitudinal axis 2321 is oriented at an offset angle Θ from, the first longitudinal axis 2320. For example, the offset angle Θ can be about 15 degrees (e.g., from 10 degrees to 20 degrees).

The extramedullary portion 2330 has a first side 136 facing radially inward (opposite the radial direction R) toward the first longitudinal axis 120 and a second side 2338 facing radially outward (in the radial direction R) away from the first longitudinal axis 120. In some embodiments, the second side 2338 has a concave surface adapted to engage a curved bone surface 413 (e.g., the medial surface of the distal portion of the first metatarsal). In other embodiments, the second side 2338 can be flat.

In some embodiments, the extramedullary portion 2330 has a tapered portion 2339 from the distal end of the beveled distal end 2316 to the proximal end of the fastener aperture 2334. The tapered portion 2339 can have a curved profile or a linear profile.

The implant 2300 can comprise any of the materials discussed above in the description of implant 100 of FIGS. 1-3. The description of these materials is not repeated, solely for brevity.

Like the implant 100 (FIGS. 1-3), the implant 2300 can be provided with a variety of offsets between the first longitudinal axis 2320 of the intramedullary portion 2310 and the second longitudinal axis 2321 of the extramedullary portion 2330. The surgeon selects the implant 2300 having the desired offset to achieve the appropriate translation for correcting the hallux valgus deformity.

In some embodiments, the intramedullary portion 2310 can be cannulated to be placed over a guide wire (not shown). During the surgery, the guide wire is driven into the cut surface of the proximal bone fragment and on the medial surface of the translated (distal) fragment.

Figure 26:
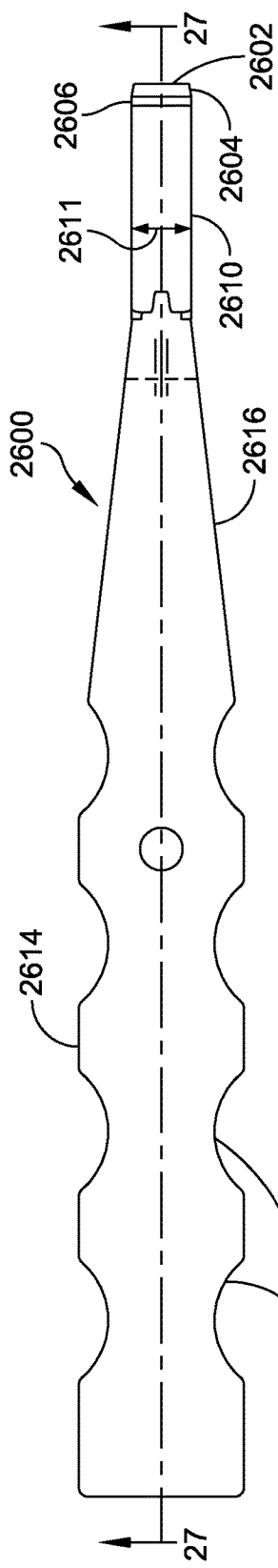
FIG. 26 is a plan view of a broach used for inserting the implant of FIG. 23.
Figure 27:
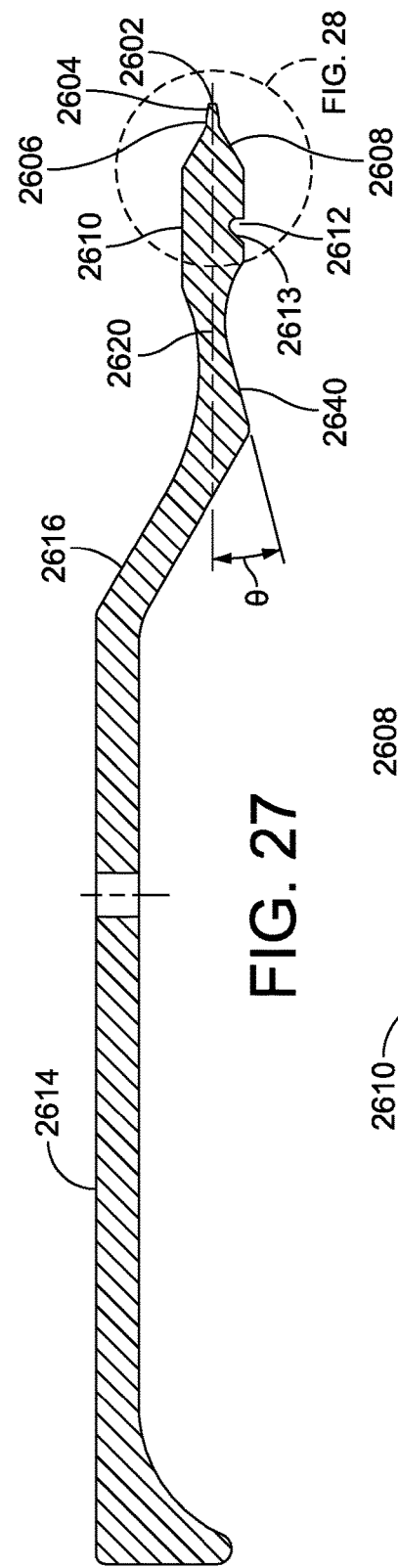
FIG. 27 is a cross-sectional view taken along section line 27-27 of FIG. 26.
Figure 28:
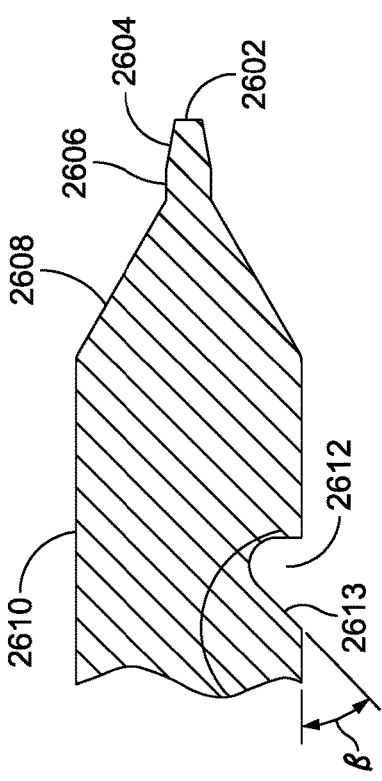
FIG. 28 is an enlarged detail of FIG. 27.

FIGS. 26-30 show a broach 2600 for forming the longitudinal opening in the proximal portion of the bone, such that the opening is adapted to receive the intramedullary portion of the implant 2300. FIG. 26 is a plan view of the broach 2600. FIG. 27 is a cross section of the broach 2600, taken along section line 27-27 of FIG. 26. FIG. 28A is an enlarged detail of FIG. 27.

The broach 2600 includes a handle 2614 and a blade 2610. The blade 2610 has a cross section with the same shape as the cross section of the intramedullary portion 2310 of the implant 2300. The blade 2610 is sized slightly (e.g., 0.001 inch) larger than the intramedullary portion 2310, so as to snugly receive the intramedullary portion 2310. For example, the intramedullary portion 2310 and blade 2610 can both be cylindrical. In one example, the intramedullary portion 2310 of the implant 2300 has a diameter of 0.252, and the blade 2610 of the broach 2600 has a diameter 2611 of 0.254. In other embodiments (not shown), the intramedullary portion 2310 and blade 2610 can both have another shape such as, but not limited to, a square.

The blade 2610 has a tapered chisel-end 2602, which can include a first tapered portion 2604, a flat portion 2606 and a second tapered portion 2608. As best seen in the embodiment of FIG. 27, the first tapered portion 2604 and the flat portion 2606 form a relatively narrow tip, similar to a flat-head screw driver, and the second tapered portion 2604 provides a smooth transition between the cylindrical blade 2610 and the flat portion 2606. In FIGS. 26-28A, the first tapered portion 2604 and the second tapered portion 2608 have planar surfaces for a linear taper. In other embodiments (not shown), the first tapered portion 2604 and the second tapered portion 2608 have curved surfaces.

Figure 29:
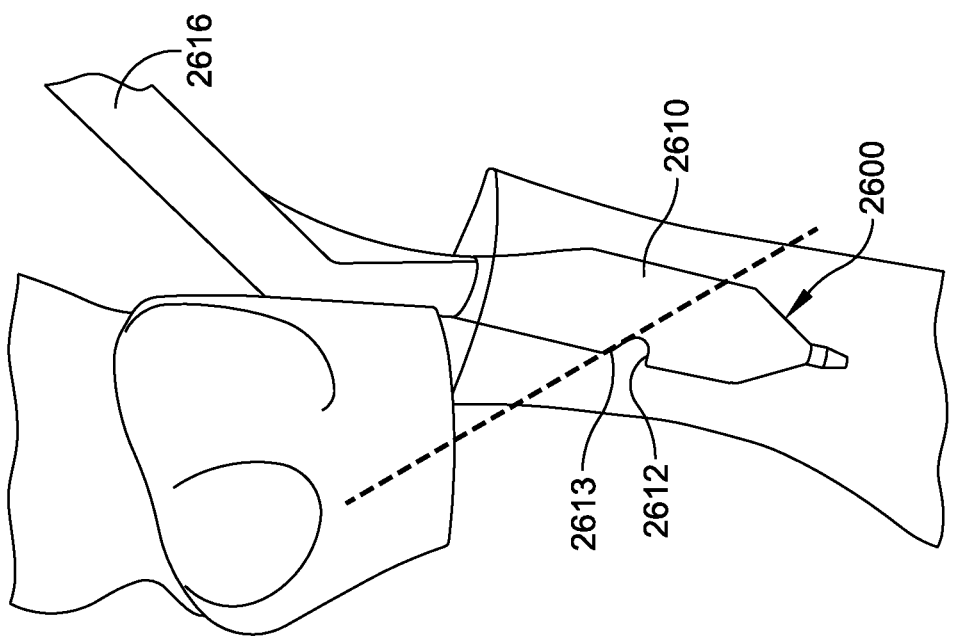
FIG. 29 shows use of the broach of FIG. 26 to form an opening in the proximal portion of a metatarsal.

The broach 2300 has an alignment feature, such as a notch 2612 or indicia (not shown), to assist in targeting a screw or nail. For example, in FIGS. 27 and 28A, a notch 2612 with a reference surface 2613 is provided. During a hallux valgus correction procedure, the surgeon can align a radiopaque elongated member (e.g., a k-wire or olive wire, not shown) with the reference surface 2613 under fluoroscopy. The reference surface 2613 and/or k-wire aligned with the reference surface 2613 can identify the axis for positioning a cross-screw (not shown) that enters the proximal portion of the bone, the aperture 2312, and the distal portion of the bone, as shown in FIGS. 29 and 30.

The broach 2600 has an abutting surface 2640 oriented at an angle Θ relative to the longitudinal axis 2620 of the broach. The angle Θ in broach 2600 can be the same as the angle Θ between the longitudinal axis 2320 of the intramedullary portion 2310 and the axis 2321 of the extramedullary portion 2330 of the implant 2300. This allows the surgeon to use the broach 2600 to position the distal portion of the metatarsal and drill the opening for the cross-screw. The surgeon can position the distal portion of the metatarsal against the surface 2640 of the broach and drill the hole for the cross-screw. Subsequently, when the broach 2600 is removed, and the implant 2300 substituted for the broach 2600, the surface 2338 of the implant 2300 abuts the medial side of the distal portion of the metatarsal, and the aperture 2312 of the implant 2300 is aligned with the cross-screw openings in the proximal and distal portions of the metatarsal. FIGS. 29 and 30 best show the relationships between surfaces of the implant 2300 and the broach 2600.

Figure 31:
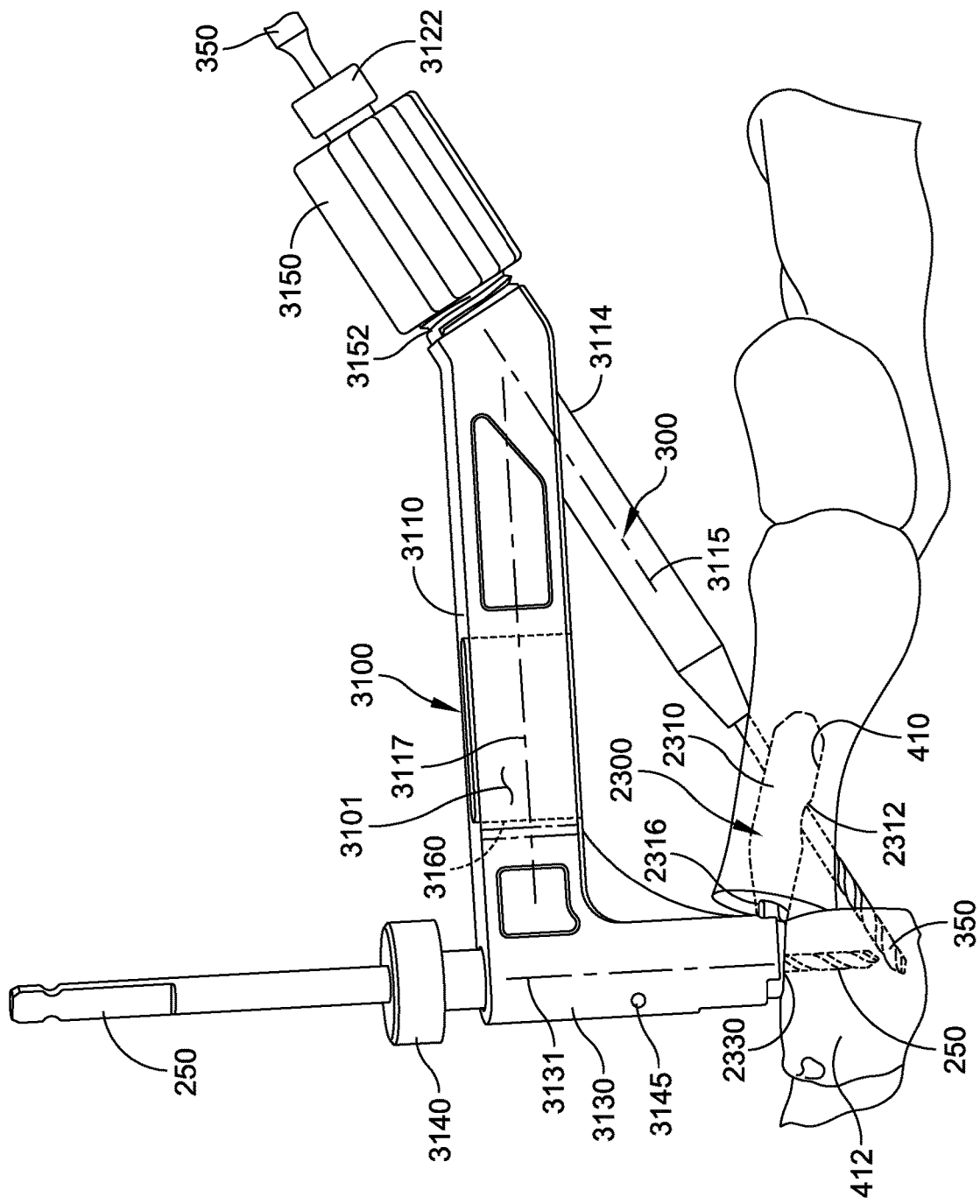
FIG. 31 is a superior view of a variation of the targeting guide.

FIG. 31 shows a variation of the target guide 200 of FIG. 12B. FIG. 31 is a plantar view of the target guide 3100. A single target guide 3100 can be used for treating hallux valgus in both right feet and left feet. FIG. 31 shows the target guide 3100 in use on a left foot 400, with the side 201 facing in the dorsal direction. When the target guide 3100 is used for treating the right foot (not shown), the target guide 3100 is flipped over, so that the side of the target guide 3100 opposite side 3101 becomes the dorsal side, and the side 3101 shown in FIG. 31 becomes the plantar side.

The target guide 3100 of FIG. 31 comprises an arm 3110 extending from a hollow cylinder 3130. The arm 3110 has a guide aperture 3114 penetrating the arm 3110 and adapted for targeting a second drill 350 for drilling a hole (inter-fragment hole) through a proximal bone section 410 and into the distal bone section 412. In some embodiments, the guide aperture 3114 is configured to receive the drill guide 300 of FIGS. 10 and 11, described above.

The body 3140 has a first longitudinal axis 3131, and the guide aperture 3114 of the arm 3110 of target guide 3100 has a second longitudinal axis 3115. The arm 3110 has a third longitudinal axis 3117, such that a plane (not shown) passes through the first longitudinal axis 3131, second longitudinal axis 3115, and third longitudinal axis 3117. The distal fastener aperture 2334 of the extramedullary portion 2330 of implant 2300 penetrates an interface surface of the extramedullary portion 2330 of the implant 2300. When the body 3140 engages the distal fastener aperture 2334 of the implant 2300, the longitudinal axis 3131 of the body 3140 is normal to the interface surface and axis 2321 of the extramedullary portion 2330.

FIG. 31 shows the drill guide 300 in situ in the target guide 3100. The arm 3110 can have a window 3160 extending from the medial surface of the arm to the lateral surface of the arm. The surgeon can insert a cutting tool (e.g., a beaver blade) through the window 3160 of the arm 3110 to make an incision in the patient's skin.

The target guide 3100 has a collet 3150 which tightens the grip of the threaded tube portion 3152 about the drill guide 300. The collet 3150 allows adjustment of the longitudinal position of the drill guide 300 within the target guide (for example, to accommodate different offsets between the distal portion 412 of the bone and the proximal portion 410 of the bone. The collet 3150 can hold the drill guide 300 in place, even in longitudinal positions where the head 3122 of the drill guide does not abut the collet 3150. To provide a compression fitting function, the threaded tube portion 3152 can have a tapered profile (not shown) with longitudinal slots (not shown) at the end of the threaded tube portion 3152. In other embodiments, the collet 3150 can have a compression ring (not shown) for gripping the drill guide 300.

The target guide 3100 can be used as a tool to position and rotate the implant 2300 and the second (distal) section 412 of the bone (e.g., first metatarsal) about the first longitudinal axis 2320 of implant 100 in situ, after the intramedullary portion 2310 of implant 2300 is inserted in a longitudinal intramedullary hole 3114 in the proximal section 410 of the bone.

In other respects, the operation of target guide 3100 is the same as described above with respect to the target guide 200 of FIG. 12B.

Figure 32:
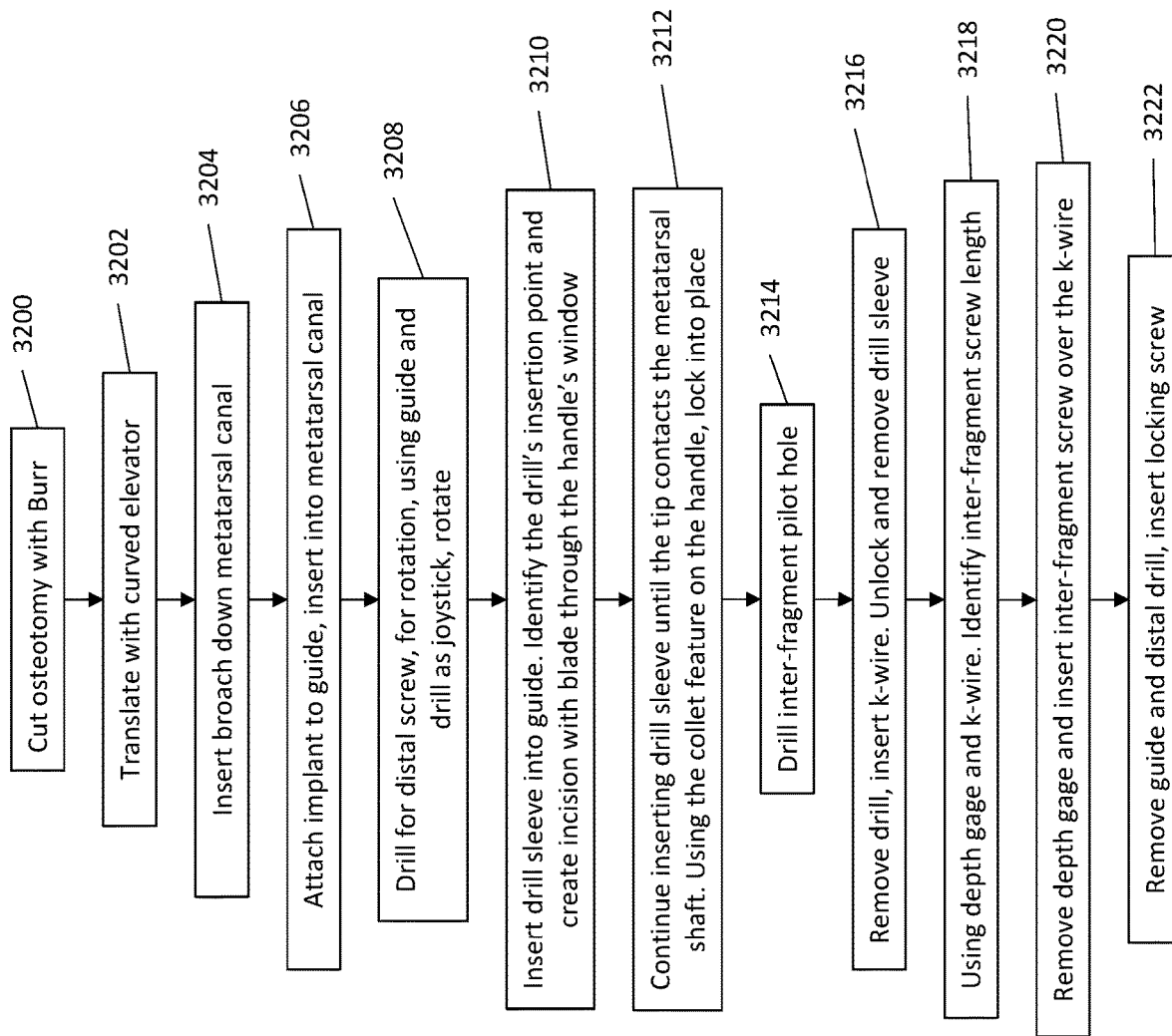
FIG. 32 is a flow chart of a method of using the implant of FIGS. 23-25, the broach of FIGS. 26-30 and the targeting guide of FIG. 31 for a minimally invasive surgery.

FIG. 32 is a flow chart of a method of using the implant 2300 of FIGS. 23-25, the broach 2600 of FIGS. 26-30 and the targeting guide 3100 of FIG. 31.

At step 3200, the surgeon cuts an osteotomy (e.g., in the first metatarsal) using a cutting tool, such as a burr.

At step 3202, the surgeon translates the distal fragment 412 of the metatarsal laterally relative to the proximal fragment 410 of the metatarsal, using a tool such as a curved elevator, for example.

At step 3204, the surgeon inserts the broach 2600 into the metatarsal canal of the proximal fragment 410 of the metatarsal, as shown in FIG. 29. The position of the distal fragment 412 can be adjusted, so the distal fragment 412 contacts the abutting surface 2640 of broach 2600. With the distal fragment 412 properly positioned, the broach 2600 can be removed from the proximal fragment.

At step 3206, the implant 2300 is attached to the targeting guide 3100. The implant 2300 is then inserted into the metatarsal canal into the position previously occupied by the broach 2600, as shown in FIG. 30. (In FIG. 30, the broach 2600 is shown in phantom.) Thus positioned, the plate portion 2330 of implant 2300 contacts the medial surface of the distal fragment 412.

At step 3208, the surgeon drills the distal hole in the distal fragment 412 to receive the distal screw. If the surgeon wishes to rotate the distal fragment 412 relative to the proximal fragment, the surgeon can use the guide 3100 and/or the drill 250 as a joystick for rotating the distal fragment 412.

At step 3210, the surgeon inserts the drill sleeve 3122 for the inter-fragment hole into the targeting guide 3100. The surgeon identifies the drill's insertion point into the bone and creates an incision in the patient's skin using a blade (e.g., a beaver blade, not shown) inserted through the window 3160 extending from the medial surface of the arm 3110 to the lateral surface of the arm 3110.

At step 3212, the surgeon continues to insert the drill sleeve 3122 through the arm 3110 until the tip of the sleeve 3122 contacts the outer surface of the proximal fragment 410 of the metatarsal, as shown in FIG. 31. The surgeon tightens the collet 3150 around the threaded tube portion 3152 to lock the drill sleeve 3122 in place.

At step 3214, guided by fluoroscopy, the surgeon drills the inter-fragment pilot hole through the proximal fragment 410 and distal fragment 412.

At step 3216, the surgeon removes the drill 350 from the inter-fragment pilot hole, inserts a k-wire, olive wire or the like (not shown) into the inter-fragment pilot hole, unlocks the collet 3150, and removes the drill sleeve 3122 from the targeting guide 3100. The k-wire or olive wire maintains the relative positions of the proximal and distal fragments 410, 412.

At step 3218, using a depth guide (not shown) and the k-wire or olive wire, the surgeon identifies the appropriate inter-fragment screw length to insert into the inter-fragment pilot hole.

At step 3220, the surgeon removes the depth gage and inserts the inter-fragment screw 450 (which can be the same as the screw 450 in FIG. 13) over the k-wire.

At step 3222, the surgeon removes the targeting guide 3100 and the distal drill 250, and inserts the distal screw 452 (which can be a locking screw 452 as shown in FIG. 13).

Figure 33:
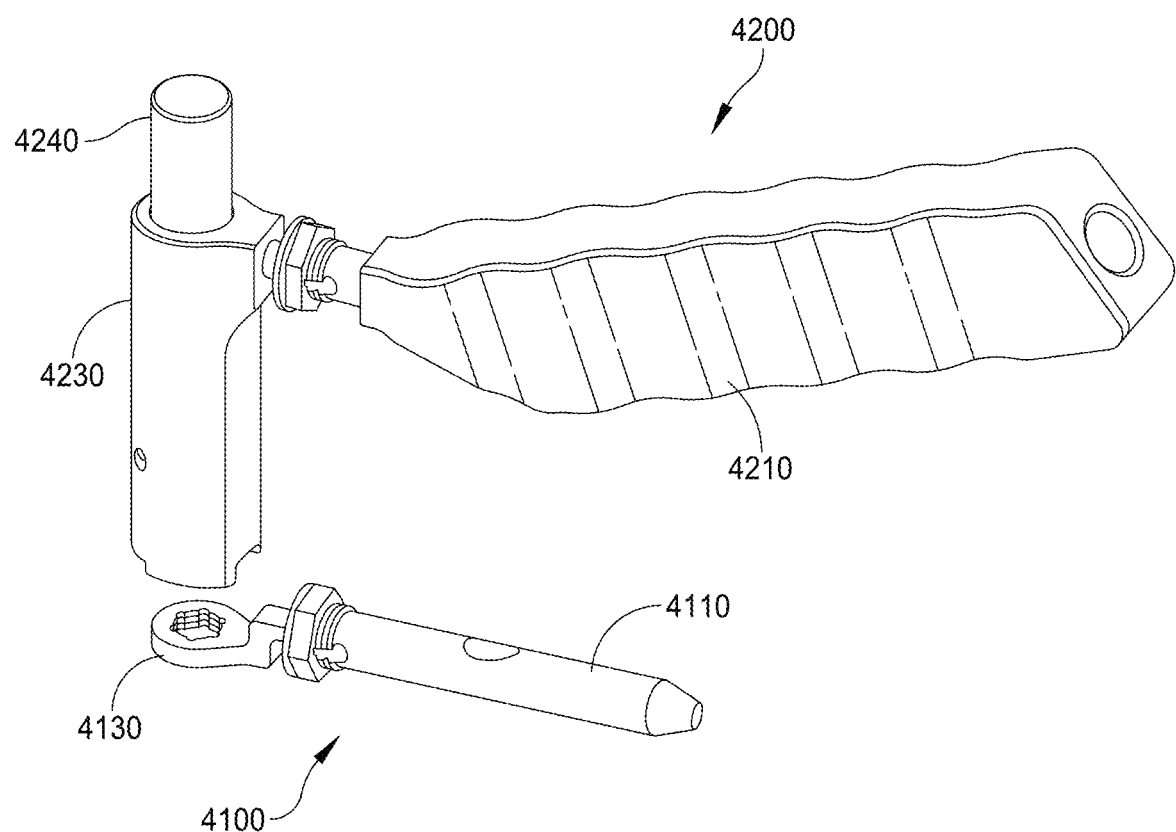
FIG. 33 is a perspective view of an implant and targeting guide according to another embodiment described herein.

FIG. 33 shows another embodiment of an implant 4100 and a target guide 4200. As will be described in further detail herein. During an operation, the target guide 4200 is coupled to the implant 4100 to allow a hole to be formed in a bone and aligned with a hole in the implant 4100. In the embodiment illustrated in FIG. 33, the extramedullary portion of the implant is able to rotate with respect to the intramedullary portion, as described in further detail below. This allows for additional adjustment of the positions of the bone sections after inserting the intramedullary portion in the first bone portion. The arm of the target guide 4200 is similarly able to rotate to allow alignment of the guide aperture of the arm with the aperture in the intramedullary portion of the implant.

Figure 34:
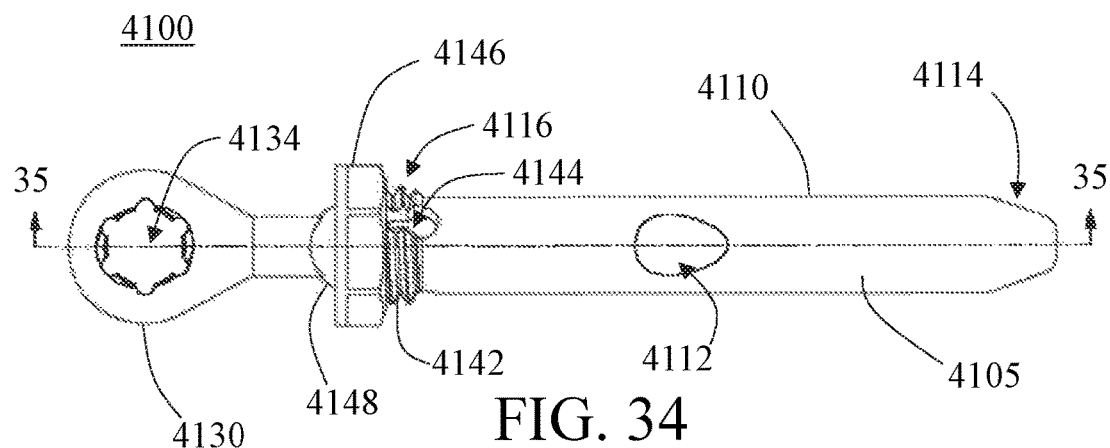
FIG. 34 is a medial view of the implant according to the embodiment shown in FIG. 33.
Figure 35:
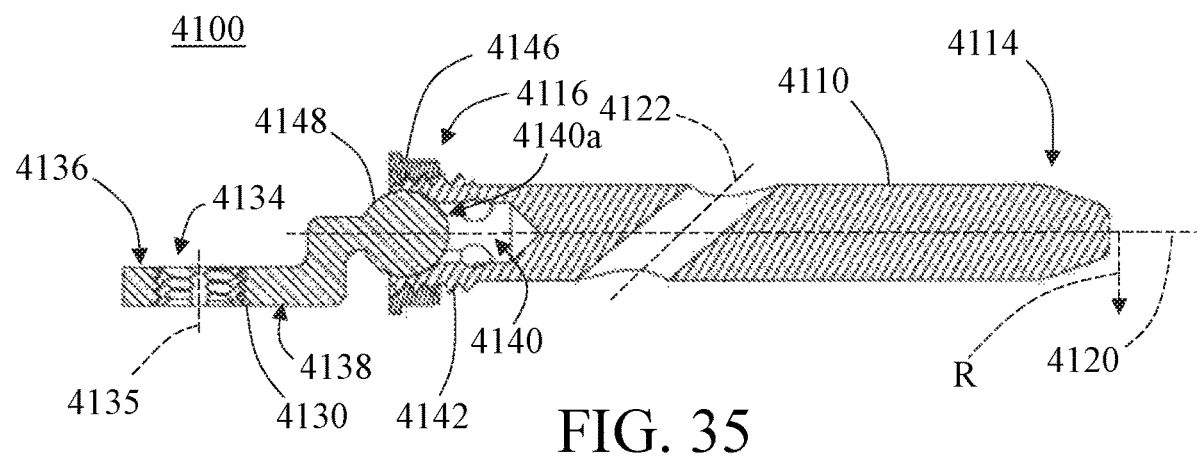
FIG. 35 is a cross-sectional view of the implant of FIG. 34 taken along section line 35-35 in FIG. 34.
Figure 42:
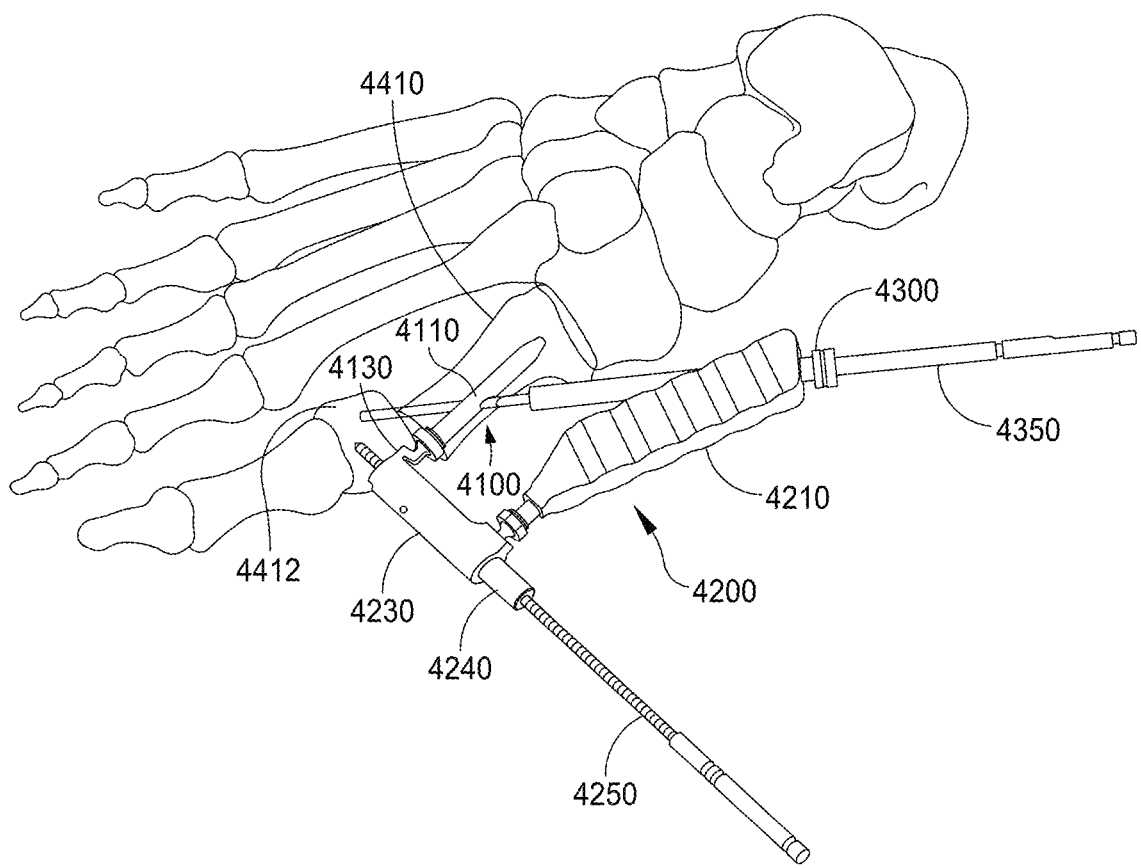
FIGS. 42 and 43 show use of the target guide of FIG. 40 in use to form proximal and distal holes for affixing the implant of FIG. 34 to bones of a foot.

FIGS. 34-39 show the implant 4100 in more detail. FIG. 34 is a top view of the implant 4100. FIG. 35 is a cross-sectional view of the implant 4100 of FIG. 34, taken along section line 34-34. Referring to FIGS. 34-35, the implant 4100 has an intramedullary portion 4110 connected to an extramedullary portion 4130. The implant 4100 is configured to attach a first bone section 4410 (FIG. 42) to a second bone section 4412 (FIG. 42). It should be noted that the implant 4100 can be used on either the left or right foot. The implant 4100 can be constructed of any of the materials described above with reference to other embodiments.

The intramedullary portion 4110 has a first longitudinal axis 4120, which can be a central axis. The intramedullary portion 4110 is configured for insertion into the first bone section 4410 (FIG. 42). The intramedullary portion 4110 can include at least one first fastener aperture 4112 having an aperture axis 4122. In some embodiments, the first aperture axis 4122 is oriented obliquely relative to the first longitudinal axis 4120. In other embodiments (not shown), the first aperture axis 4122 is orthogonal to the first longitudinal axis. The at least one first fastener aperture 4112 is configured to receive a nail, screw, k-wire or rod to couple the implant 4100 to the first 4410 and/or second 4412 bone sections, as described herein in connection with other embodiments.

The extramedullary portion 4130 is configured to abut a surface of the second bone section 4412 (FIG. 42). The extramedullary portion 4130 includes at least one second (distal) fastener aperture 4134 disposed to receive a bone fastener (e.g., an "Ortholoc® 3DiTM" locking screw sold by Wright Medical Technology, Inc. of Memphis, TN), inserted in the second bone section 4412. The bone fastener may be disposed transversely or obliquely, relative to the fastener aperture 4134. In some embodiments, polyaxial screws can be inserted with an angle of 0.0 to about 15 degrees from a second aperture axis 4135 of the second (distal) fastener aperture 4134. In some embodiments, polyaxial screws such as 3Di locking screws or non-locking screws sold by Wright Medical Technology, Inc. of Memphis, TN may be utilized.

In some embodiments, the extramedullary portion 4130 is radially offset from the longitudinal axis 4120 in a radial direction R. In such embodiments, the extramedullary portion 4130 has a first side 4136 facing radially inward (opposite the radial direction R) toward the first longitudinal axis 4120 and a second side 4138 facing radially outward (in the radial direction R) away from the first longitudinal axis 4120. In some embodiments, the second side 4138 has a concave surface adapted to engage a curved bone surface.

In some embodiments, the intramedullary portion 4110 comprises a cylinder or cylindrical shaft having an outer surface 4105, and the extramedullary portion 4130 is joined to the intramedullary portion 4110 so that a portion of the outer surface 4105 is located between the first side 4136 of the extramedullary portion 4130 and the second side 4138 of the extramedullary portion 4130. That is, the first side 4136 can be located radially inward from the surface 4105, and the second side 4138 can be located radially outward from the surface 4105. As described with respect to other embodiments, the offset between the first longitudinal axis 4120 of the intramedullary portion 4110 and the first side 4136 of the extramedullary portion 4130 can have a variety of values, each corresponding to a different amount of translation (also referred to as "shifting") of the first bone.

In some embodiments, the intramedullary portion 4110 has a tapered proximal end 4114. The tapered proximal end 4114 facilitates insertion of the implant 4100 into a longitudinal hole in the first (proximal) section 4410 of the bone.

The intramedullary portion 4110 is coupled to the extramedullary portion 4130 such that the extramedullary portion 4130 can rotate with respect to the intramedullary portion 4110. This allows for adjustment of the extramedullary portion 4130 during a procedure, thereby allowing for adjustment of the first bone section 4410 and the second bone section 4412.

For example, the intramedullary portion 4110 can include a socket 4140 at its distal end 4116. The intramedullary portion 4110 can further include a plurality of collet arms 4142 surrounding the socket 4140, the collet arms 4142 each separated from one another by slots 4144. In various embodiments, the collet arms 4142 can include threads on their exterior surface. The implant 4100 can further include a collet nut 4146 configured to engage the threads.

The extramedullary portion 4130 includes an engagement portion 4148 (e.g., a spherical portion or ball) configured to be received in the socket 4140 of the intramedullary portion 4110. In some embodiments, the socket 4140 can include a spherical recess 4140a configured to receive the engagement portion 4148 of the extramedullary portion 4130. With the engagement portion 4148 of the extramedullary portion 4130 disposed in the socket 4140, rotation of the collet nut 4146 in a first direction (e.g., clockwise) causes the collet arms 4142 to move inward to clamp the engagement portion 4148 to restrict rotation of the extramedullary portion 4130 with respect to the intramedullary portion 4110. Further, rotation of the collet nut 4146 in a second, opposite direction (e.g., counter-clockwise) allows the collet arms 4142 to flex radially outward toward their natural position to loosen the engagement with the engagement portion 4148 to allow rotation of the extramedullary portion 4130 with respect to the intramedullary portion 4110.

Figure 36:
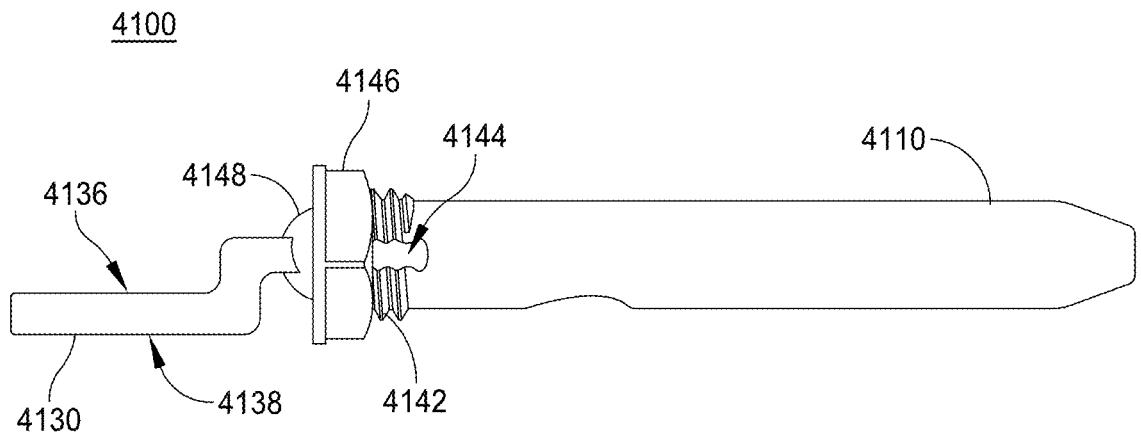
FIG. 36 is an inferior view of the implant of FIG. 34 with the extramedullary portion in a first rotational position.
Figure 37:
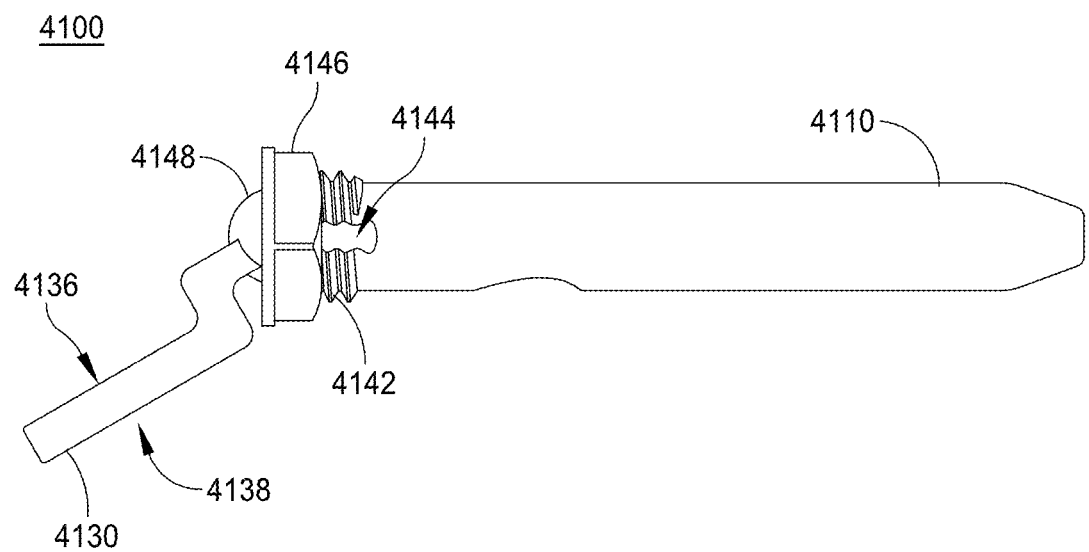
FIG. 37 is an inferior view of the implant of FIG. 34 with the extramedullary portion in a second rotational position.
Figure 38:
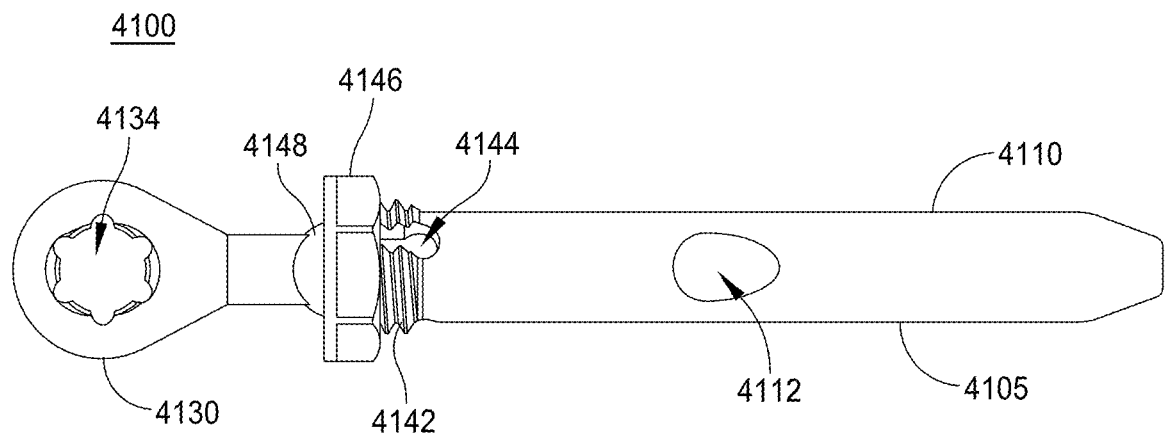
FIG. 38 is a medial view of the implant of FIG. 34 with the extramedullary portion in a first rotational position.
Figure 39:
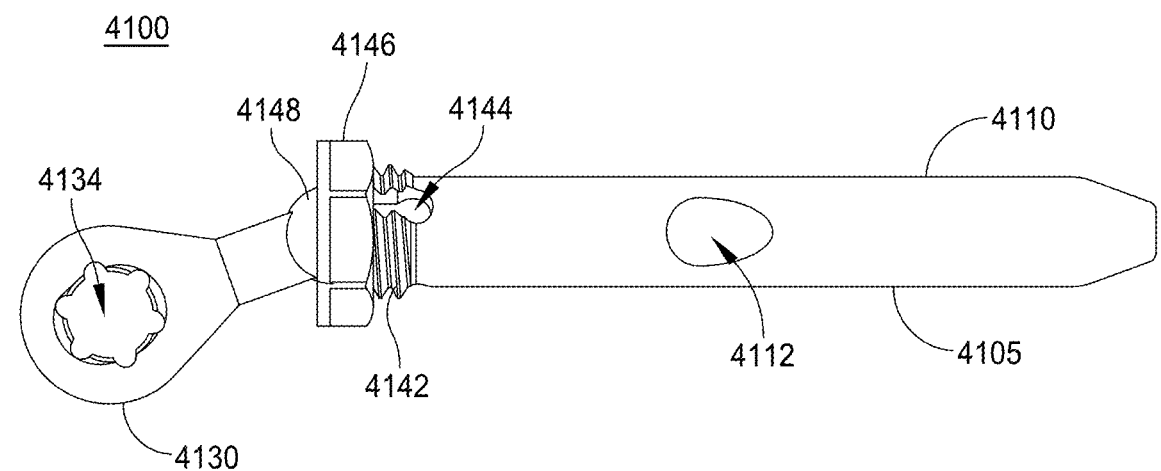
FIG. 39 is a medial view of the implant of FIG. 34 with the extramedullary portion in a second rotational position.

FIGS. 36-39 show examples of rotation of the extramedullary portion 4130 relative to the intramedullary portion 4110. In various embodiments, the extramedullary portion 4130 may be able to rotate around a variety of axes, similarly to a ball and socket joint. For example, as shown in FIGS. 36 and 37, the extramedullary portion 4130 can rotate about a superior-inferior axis when implanted as shown in FIG. 42. Further, as shown in FIGS. 38 and 39, the extramedullary portion 4130 can rotate about a medial-lateral axis when implanted as shown in FIG. 42. It should be understood that these are just exemplary rotational directions and the extramedullary portion 4130 can rotate around a variety of desired axes as with a ball and socket joint.

Figure 40:
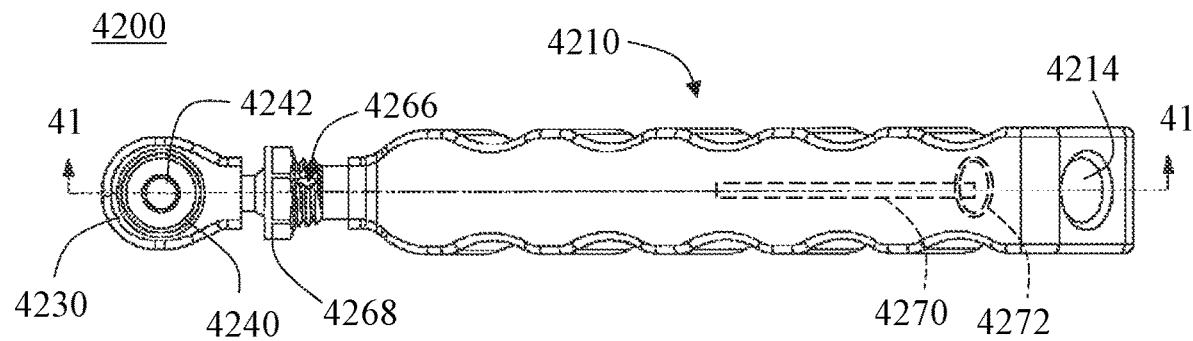
FIG. 40 is a medial view of the targeting guide according to the embodiment shown in FIG. 33.
Figure 41:
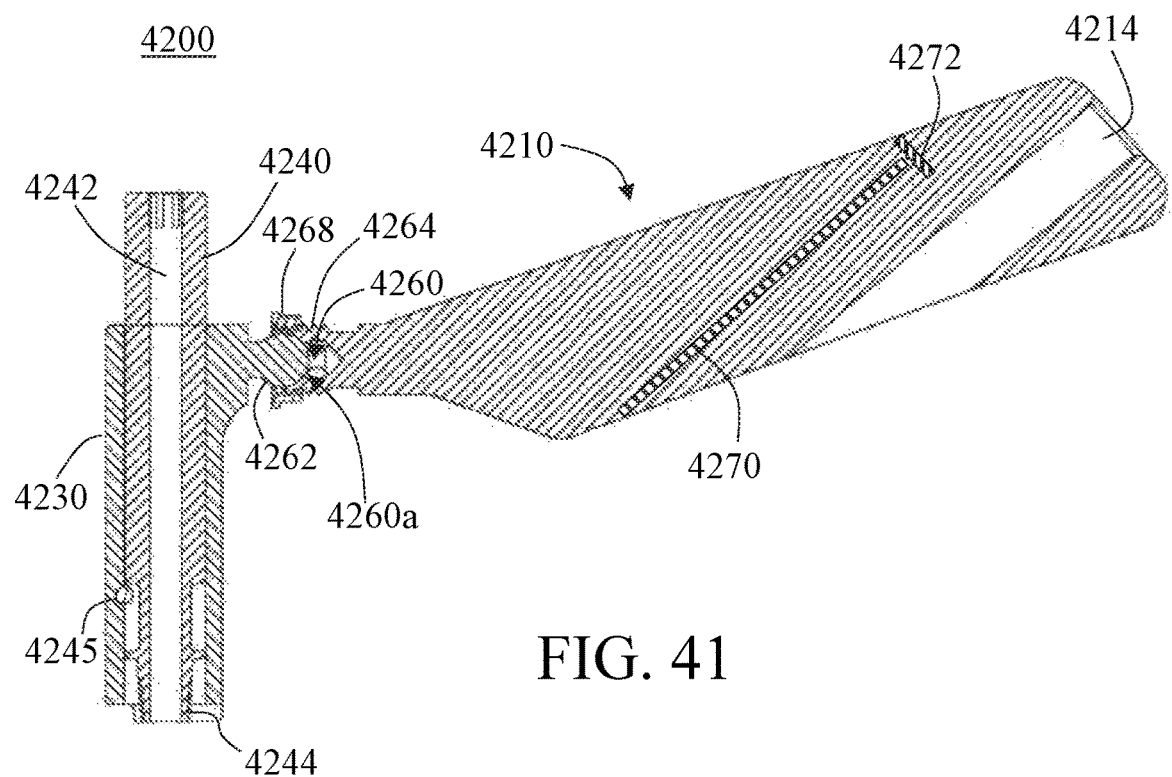
FIG. 41 is a cross-sectional view of the targeting guide of FIG. 40 taken along section line 41-41 in FIG. 40.

FIGS. 40 and 41 show the target guide 4200. FIG. 40 is a top view and FIG. 41 is a cross-sectional view taken at section line 41-41. The target guide 4200 can be similar in many aspects to the target guide 200 described above. In the embodiment shown in FIGS. 40 and 41, the arm 4210 is coupled to the cylinder 4230 such that the arm 4210 can rotate with respect to the cylinder 4230. This may allow the arm 4210 to be rotated to align the guide aperture 4214 with the first fastener aperture 4112 during a procedure. Still referring to FIGS. 40 and 41, fluoroscopic alignment markers 4270, 4272 may be located within the arm 4210 of the target guide 4200 for fluoroscopic adjustment of the arm and alignment of the guide aperture 4214 with the first fastener aperture 4112. Once position and alignment is confirmed, the collet nut 4268 is tightened to hold an aligned axis between the guide aperture 4214 and the fastener aperture 4112.

The arm 4210 can be coupled to the cylinder 4230 in any manner to allow rotation of the arm 4210 with respect to the cylinder 4230. For example, as shown in FIGS. 40 and 41, the arm 4210 can define a socket 4260 configured to a receive a spherical engagement portion 4262 extending from the cylinder 4230. The socket 4260 can define a spherical recess 4260a configured to receive the engagement portion 4262. The arm 4210 can include a plurality of collet arms 4264 defining the socket 4260, with each collet arm 4264 separated by a slot 4266. The target guide 4200 can further include a collet nut 4268 coupled to the threads of the collet arms 4264 such that rotation of the collet nut 4268 in a first direction causes the collet arms 4264 to flex inward to grip the engagement portion 4262 to restrict rotation of the arm 4210 relative to the cylinder 4230. Further, rotation of the collet nut 4268 in a second, opposite direction allows the collet arms 4264 to flex outward toward their natural, unstressed position to loosen the grip on the engagement portion 4262 to allow rotation of the arm 4210 with respect to the cylinder 4230.

Figure 43:
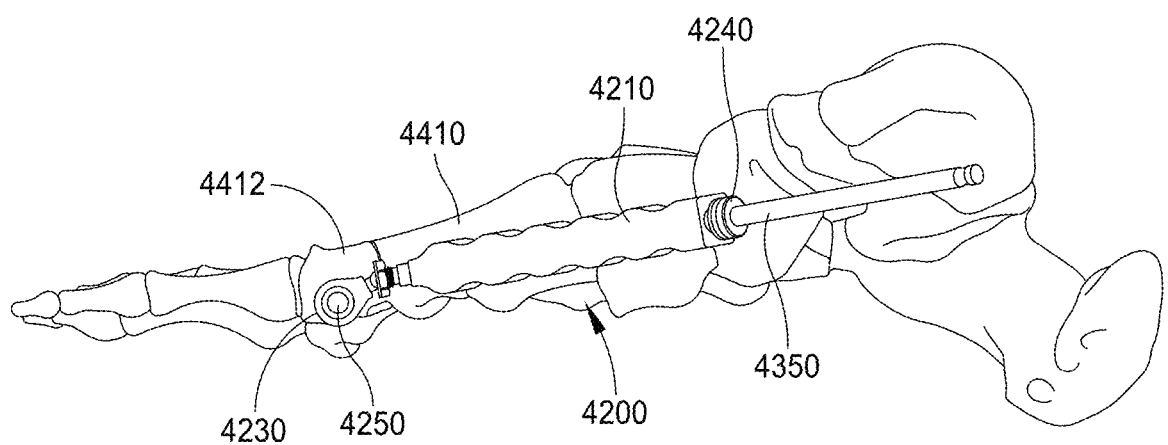

FIGS. 42 and 43 show the implant 4100 and target guide 4200 in use. As shown, the intramedullary portion 4110 of the implant 4100 is inserted into the first bone section 4410. The target guide 4200 is coupled to the extramedullary portion 4130 (e.g., via threaded portion 4244 of body 4240 shown in FIG. 41). A drill 4250 can be inserted through the central longitudinal passage 4242 of a body 4240 that is coupled to the target guide 4200 (e.g., using a pin 4245, as described with respect to other embodiments) to form a hole in the second bone section 4412 to receive a screw inserted through the fastener aperture 4134. In addition, a drill guide 4300 is placed in the guide aperture 4214 of the target guide 4200 and a second drill 4350 is inserted through the drill guide 4300 to form a hole in the first bone section 4410 for receiving a screw. In some embodiments, the second drill 4350 forms a hole through the first bone section 4410 and into the second bone section 4412 such that an inter-fragment screw can be used, as described above. The drill guide 4300 may also be used for fluoroscopic alignment of the guide aperture 4214 and fastener aperture 4112 prior to locking the collet nut 4268.

Figure 44:
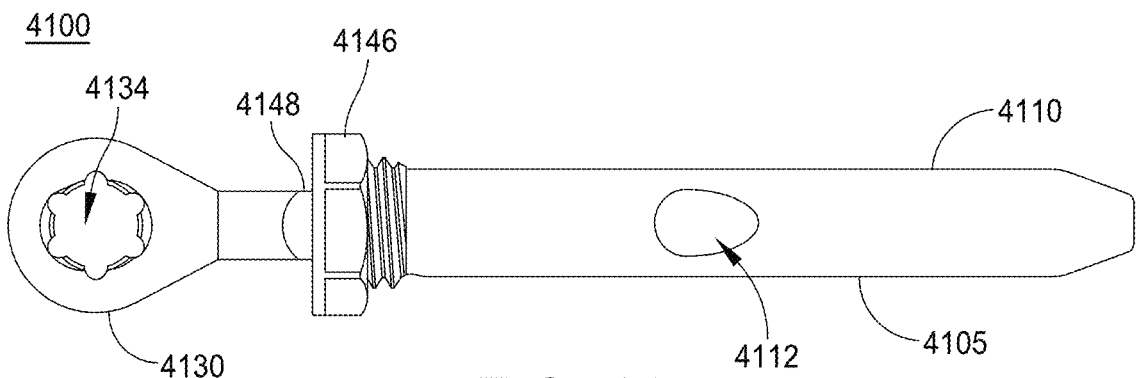
FIG. 44 is a medial view of an implant according to another embodiment described herein.
Figure 45:
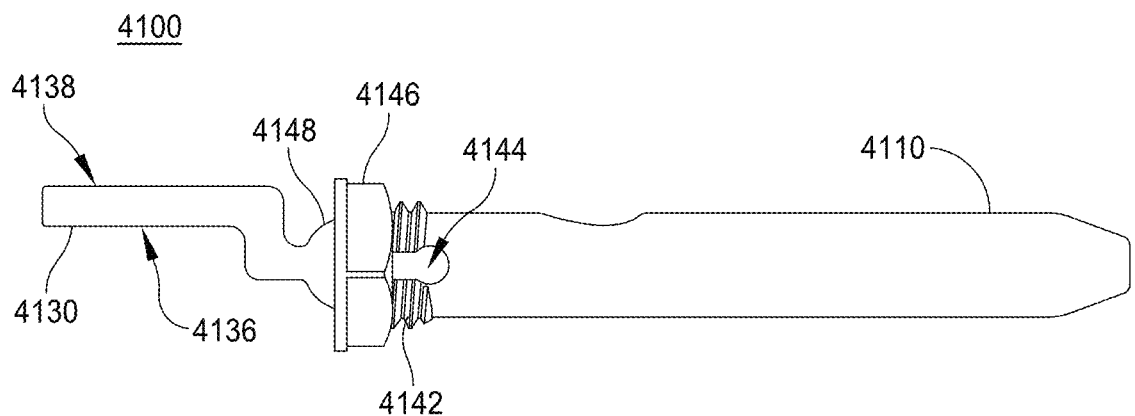
FIG. 45 is a superior view of the implant of FIG. 44 with the extramedullary portion in a first rotational position.
Figure 46:
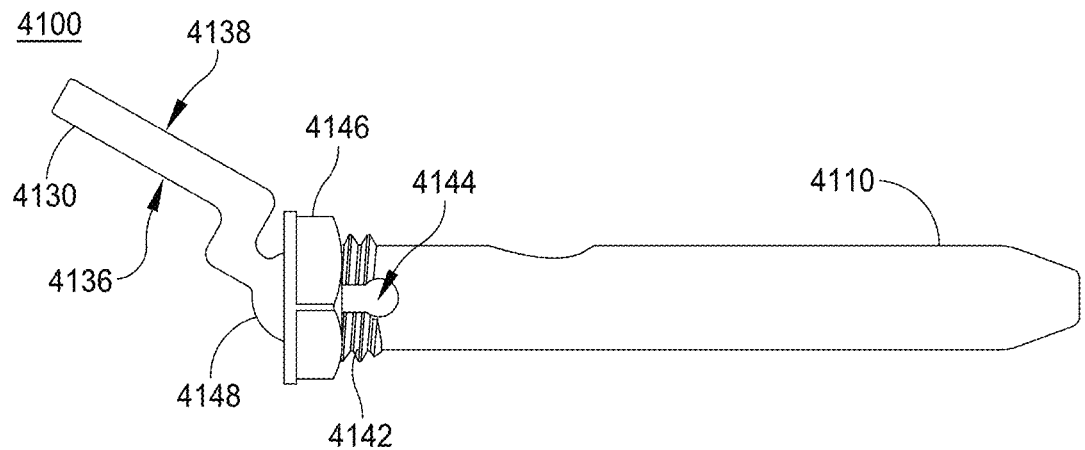
FIG. 46 is a superior view of the implant of FIG. 45 with the extramedullary portion in a second rotational position.

FIG. 44 shows a top view of another embodiment of the implant 4100. In this embodiment, the implant 4100 is configured such that the extramedullary portion 4130 is only able to rotate about a substantially superior-inferior axis when the implant 4100 is implanted, as shown in FIGS. 45 and 46. This may allow adjustment of the bone sections in the medial-lateral direction, but not in the platarflexion-dorsiflexion direction. In such embodiments, the engagement portion 4148 of the extramedullary portion 4130 can include flat superior and inferior sides that restrict the extramedullary portion 4130 to rotate in only a single plane. The socket 4140 of the intramedullary portion 4110 can include complementary flat surfaces to accommodate the engagement portion 4148.

Figure 47:
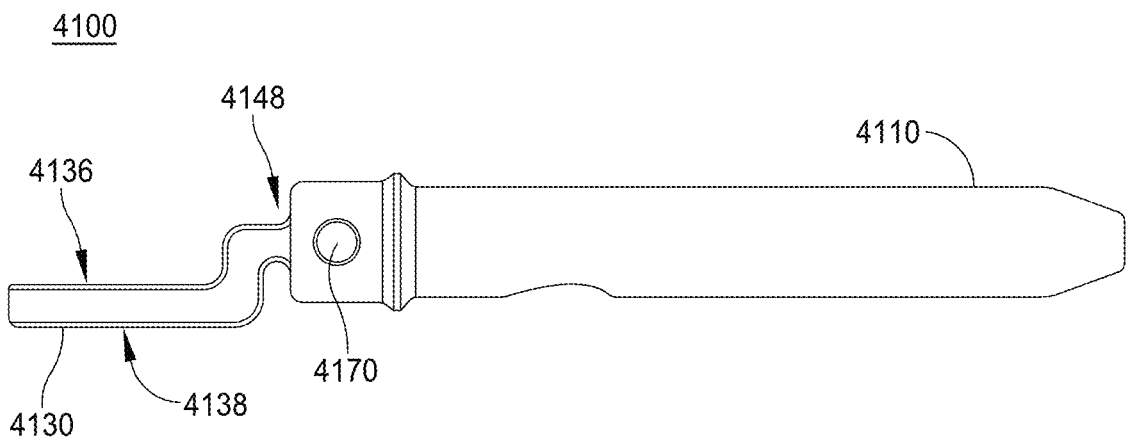
FIG. 47 is an inferior view of an implant according to another embodiment described herein, with the extramedullary portion in a first rotational position.
Figure 48:
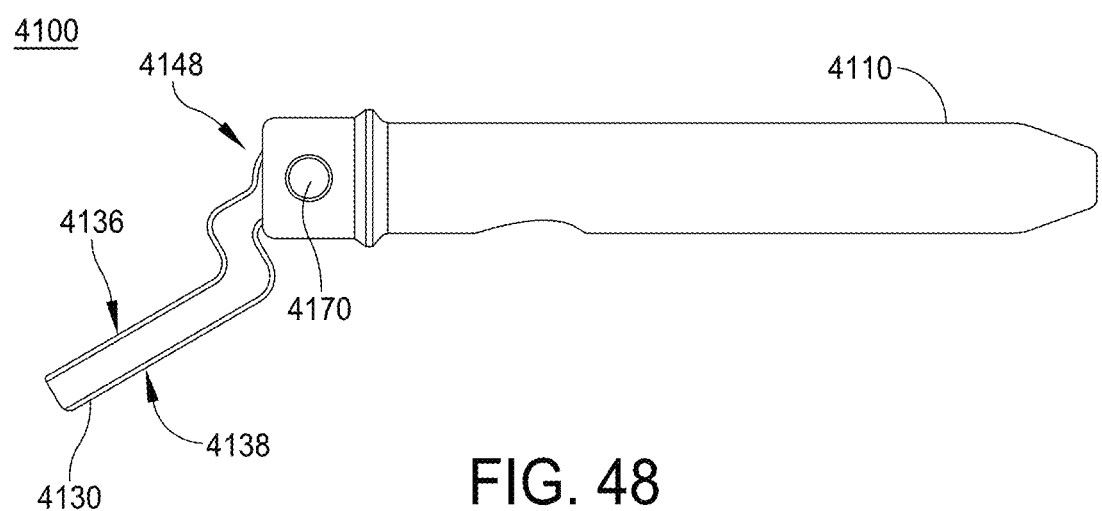
FIG. 48 is an inferior view of the implant of FIG. 47 with the extramedullary portion in a second rotational position.

FIGS. 47 and 48 show another embodiment of the implant 4100. In this embodiment, the engagement portion 4148 of the extramedullary portion 4130 is coupled to the intramedullary portion 4110 with a pin 4170. The pin 4170 may be oriented orthogonally to a plane that includes the distal fastener aperture axis 4135 and the longitudinal axis 4120 (shown in FIG. 35) of the intramedullary portion 4110. In other words, the pin 4170 can be oriented in a substantially superior-inferior orientation when the implant 4100 is implanted. The extramedullary portion 4130 is able to rotate around the pin 4170 (e.g., in a medial-lateral direction).

Figure 49:
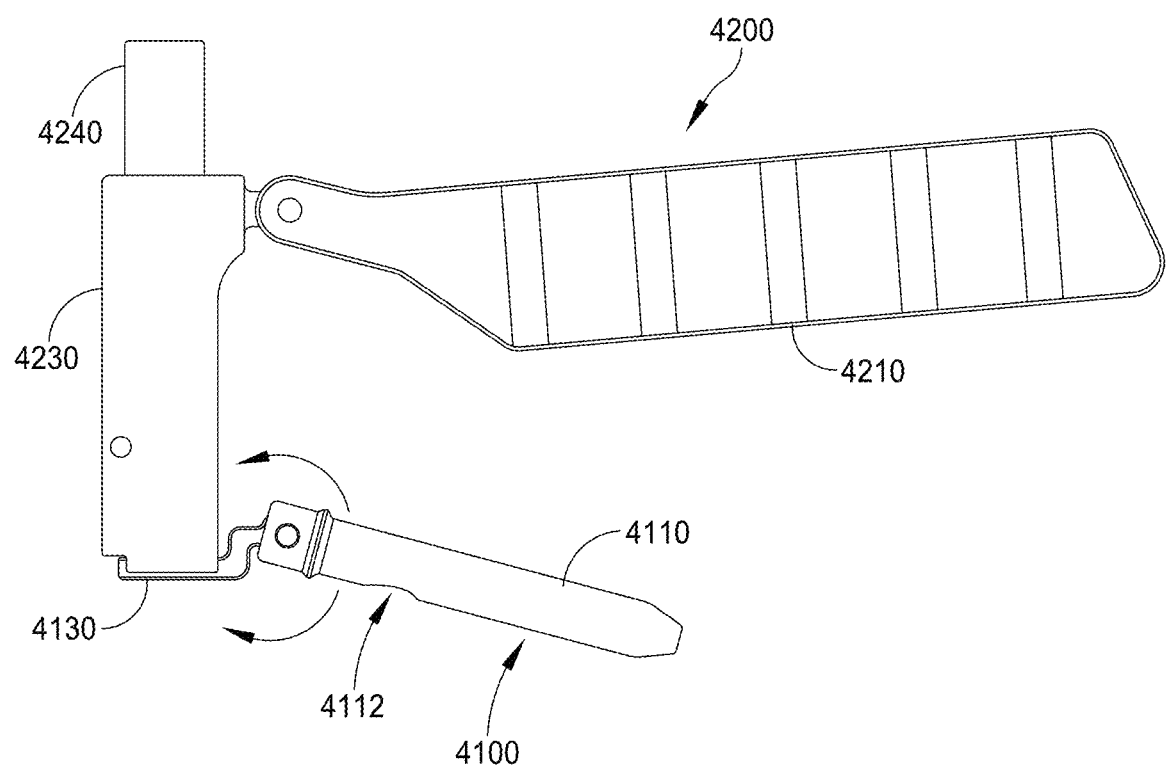
FIG. 49 is an inferior view of the implant of FIG. 47 attached to a target guide according to an embodiment described herein.

FIG. 49 shows the implant 4100 coupled to an embodiment of the target guide 4200. In this embodiment, the arm 4210 of the target guide 4200 is limited to rotating with respect to the cylinder 4230 about an axis that is substantially parallel to the pin 4170 of the implant 4100 to allow alignment of the guide aperture 4214 with the proximal fastener aperture 4112 in the intramedullary portion 4110.

While the embodiments of the implant in which the extramedullary portion is rotatable with respect to the intramedullary portion are shown having a single aperture in the extramedullary portion, it should be understood that the extramedullary portion can include two or more apertures, such as in the embodiments shown in FIGS. 14-16, 17-19, and 20-22. Further, embodiments of the implant with a rotatable extramedullary portion can include a cannula as shown in the embodiment shown in FIGS. 17-19.

Although the examples of intramedullary portions 110, 1410, 1510, 1810, 2310, 4110 of respective implants 100, 1400, 1500, 1800, 2300, 4100 are shown as having circular cross-sections, any of the intramedullary portions 110, 1410, 1510, 1810, 2310, 4100 can have a different cross-sectional shape, such as an ellipse, a triangle, a rectangle, or other polygon. Any of these embodiments can be implemented with our without a slot (FIG. 17) or longitudinal cannula.

In some embodiments, the implant is inserted using the targeting guide, and its position and rotation angle are maintained by a screw. In other embodiments (not shown), the intramedullary portion is expandable. For example, the intramedullary portion can have an expandable (e.g., flared) portion and an expander (e.g., cone) portion that radially expands the expandable portion when the expandable and expander portions are driven together. Alternatively, the intramedullary portion can have a molly bolt mechanism. In other embodiments, the expansion is provided by phase change of a shape-memory material, such as nitinol.

Figure 50:
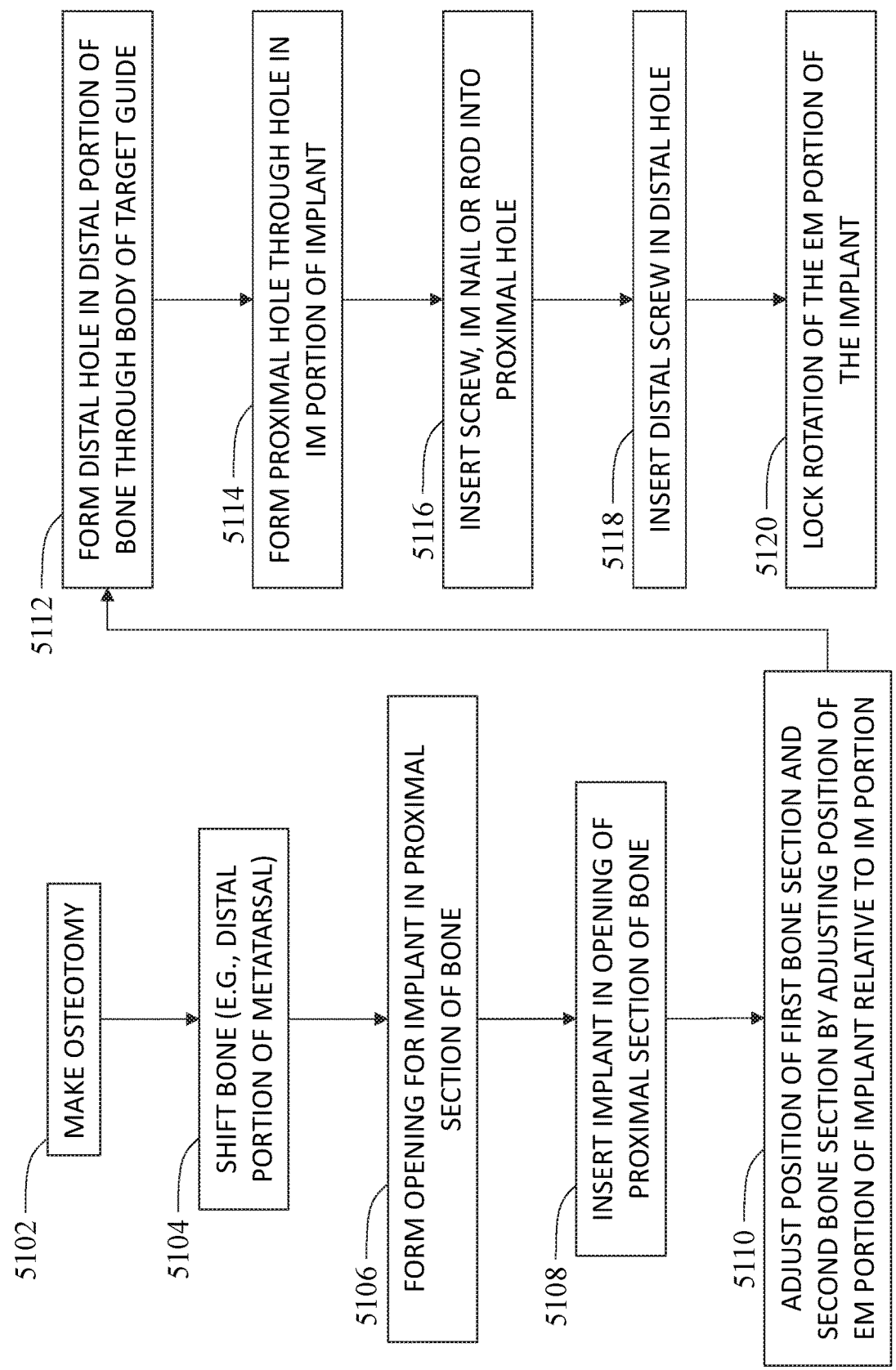
FIG. 50 is a flow chart of a method of using the implants and target guides of FIGS. 33-49.

FIG. 50 is a flowchart illustrating a method of implanting an implant (e.g., implant 4100). At step 5102, the surgeon performs an osteotomy to separate a bone into proximal and distal sections. For example, the surgeon can perform a transverse osteotomy to separate a first metatarsal into a proximal section and a distal section.

At step 5104, the surgeon shifts one of the bone sections, so a nearest medial edge of the distal section is offset from the first longitudinal axis. For example, the surgeon can move the distal section of the first metatarsal in the lateral direction to expose at least a portion of the cut (anterior) surface of the proximal section of the first metatarsal.

At step 5106, the surgeon forms an opening in the proximal section of the bone for receiving the intramedullary portion of the implant. The opening can be formed using any of the methods described herein, including, for example, a k-wire and cannulated drill or a broach.

At step 5108, the surgeon inserts the intramedullary portion of the implant into the longitudinal intramedullary opening in the proximal section of the first metatarsal. During the insertion, the surgeon may grip the arm of the target guide to push the implant into the opening.

At step 5110, the surgeon adjusts the position of the first bone section and second bone section by adjusting the position of the extramedullary portion of the implant relative to the extramedullary portion. This can include rotating the extramedullary portion relative to the extramedullary portion, for example, about an axis that is oriented substantially superiorly-inferiorly. It should be understood that this can be performed before or after inserting screws or other fasteners to attach the implant to the first and second bone sections.

At step 5112, the surgeon forms a distal hole in the distal section of the bone through the body of the target guide. The distal hole can be formed in any appropriate manner, including for example with a reamer or drill.

At step 5114, the surgeon forms a proximal hole in the proximal section of the bone through the hole in the intramedullary portion of the implant. In some embodiments, this hole is an interfragment hole that extends through the proximal section of the bone and into the distal section of the bone. The proximal hole can be formed in any appropriate manner including, for example, with a drill guide and drill or reamer.

At step 5116, the surgeon inserts a screw, nail, rod, or k-wire into the proximal hole and through the intramedullary portion of the implant to secure the implant to the proximal section of the bone.

At step 5118, the surgeon inserts a distal screw in the distal hole and engages the screw with the aperture in the extramedullary portion of the implant.

Optionally, at step 5120, the surgeon locks rotation of the extramedullary portion of the implant relative to the intramedullary portion of the implant. For example, the surgeon can rotate a collet nut to tighten collet arms of the intramedullary portion on an engagement portion of the extramedullary portion. It should be understood that in some embodiments, the rotation of the extramedullary portion may not need to be locked. For example, if an interfragmentary screw is used, the interfragmentary screw may restrict relative movement of the first bone portion and the second bone portion.

Although the subject matter has been described in terms of exemplary embodiments, it is not limited thereto. Rather, the appended claims should be construed broadly, to include other variants and embodiments, which may be made by those skilled in the art.

What is claimed is:

1. An implant configured to attach a first bone section to a second bone section, the implant comprising:
   an intramedullary portion configured for insertion into the first bone section and including a proximal insertion end and a distal end that includes a socket; and
   an extramedullary portion configured to abut a surface of the second bone section and including a first fastener aperture configured to receive a bone fastener inserted in the second bone section and a ball configured to engage the socket to couple the intramedullary portion and the extramedullary portion;
   wherein the intramedullary portion and the extramedullary portion are coupled such that the extramedullary portion is rotatable with respect to the intramedullary portion.

2. The implant of claim 1, wherein the intramedullary portion includes a second fastener aperture extending therethrough.

3. The implant of claim 2, wherein the second fastener aperture is adapted to receive a locking fastener.

4. The implant of claim 1, wherein the at least one first fastener aperture is configured to receive a nail, screw, k-wire or rod extending therethrough.

5. The implant of claim 1, wherein the socket is configured to receive the ball to couple the intramedullary portion and the extramedullary portion.

6. The implant of claim 5, further comprising a nut and wherein the intramedullary portion includes a plurality of threaded collet arms, the plurality of collet arms at least partially defining the socket, and wherein rotation of the nut in a first direction clamps the collet arms to the ball of the extramedullary portion to restrain rotation of the extramedullary portion relative to the intramedullary portion.

7. The implant of claim 1, wherein
   the intramedullary portion extends from a first end to a second end and a first longitudinal axis extends from the first end to the second end and through the ball when the intramedullary portion and the extramedullary portion are coupled, and
   the extramedullary portion includes a second longitudinal axis that is parallel to, and offset from, the first longitudinal axis.

8. The implant of claim 1, wherein the extramedullary portion has a first side facing radially inward toward a longitudinal axis of the intramedullary portion and one second side facing radially outward from the longitudinal axis, the second side having a concave surface adapted to engage a curved bone surface.

9. The implant of claim 1, wherein
the extramedullary portion has a first side facing radially inward toward a longitudinal axis of the intramedullary portion and a second side facing radially outward from the longitudinal axis, and
the first side and the second side are flat.

10. An implant comprising:
an intramedullary portion configured for insertion into a first bone and including:
an elongated body extending along a centrally located first longitudinal axis;
a first fastener aperture through the body, centered on the longitudinal axis, and configured to receive a bone fastener extending therethrough; and
a proximal end that is tapered; and
an extramedullary portion configured to abut a surface of a second bone and including:
a circular end; and
a second fastener aperture through the circular end and configured to receive a bone fastener extending therethrough, wherein
the implant is configured such that the intramedullary portion and the extramedullary portion are bendable relative to each other.

11. The implant of claim 10, wherein the first fastener aperture is configured to receive a locking fastener.

12. The implant of claim 10, wherein the second fastener aperture is configured to receive a locking fastener.

13. The implant of claim 10, wherein a first aperture axis though the first fastener aperture is oriented obliquely relative to the first longitudinal axis.

14. The implant of claim 10, wherein a second aperture axis though the second fastener aperture is oriented orthogonal relative to the first longitudinal axis.

15. The implant of claim 10, wherein the extramedullary portion has a flat first side and a second side opposite from the first side that has a concave surface adapted to engage a curved bone surface.

16. The implant of claim 10, wherein a second longitudinal axis through the extramedullary portion is offset from the first longitudinal axis.

17. The implant of claim 10, further comprising a ball and socket joint between the intramedullary portion and the extramedullary portion.

* * * * *